United States Patent
Gross et al.

(10) Patent No.: US 6,939,963 B2
(45) Date of Patent: Sep. 6, 2005

(54) METHOD FOR THE PREPARATION OF SELECTIVELY-SUBSTITUTED CORROLES AND NEW SUBSTITUTED CORROLES

(75) Inventors: Zeev Gross, Petach Tikva (IL); Atif Mahammed, Muawyia Village (IL); Irena Saltsman, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 10/482,690

(22) PCT Filed: Jul. 1, 2002

(86) PCT No.: PCT/IL02/00536
§ 371 (c)(1), (2), (4) Date: Jan. 2, 2004

(87) PCT Pub. No.: WO03/004021
PCT Pub. Date: Jan. 16, 2003

(65) Prior Publication Data
US 2004/0180872 A1 Sep. 16, 2004

Related U.S. Application Data

(60) Provisional application No. 60/301,851, filed on Jul. 2, 2001.

(51) Int. Cl.⁷ .......................................... C07D 487/22
(52) U.S. Cl. ....................................... 540/145; 540/471
(58) Field of Search ................................. 540/145, 471

(56) References Cited

FOREIGN PATENT DOCUMENTS

WO    WO-00/18771    4/2000

*Primary Examiner*—Richard L. Raymond
*Assistant Examiner*—Jason H. Johnsen
(74) *Attorney, Agent, or Firm*—Browdy and Neimark, P.L.L.C.

(57) ABSTRACT

Corroles of formula I, wherein Ar is aryl or heteroaryl; M is absent or is a metal selected from Al, Ga, Co, Mn, Fe, Ru, Sn, Cr or Rh; $E_2$, $E_3$ and $E_{17}$, the same or different, each is H, $SO_2Cl$, $SO_3H$, $SO_2NR_1R_2$, $CO_2H$, $CO_2R$, $COC_1$, $CONR_1R_2$, CHO or $NO_2$, R is alkyl or aryl, and $R_1$ and $R_2$, the same or different, each is H, alkyl, aryl or together with the N atom to which they are attached form a saturated 5–6 membered ring optionally containing a further heteroatom selected from O, S and N; and $E_{18}$ is H or CHO; or $E_3$ and $E_{18}$ are H and $E_2$ and $E_{17}$ are each $SO_2$, both $SO_2$ groups being linked by a bridge $R_3N(R_4)$-phenyl-$(R_4)NR_3$, wherein $R_3$ is H, alkyl, phenyl or aralkyl, and $R_4$ is alkylene; and provided that at least one of $E_2$, $E_3$, $E_{17}$ and $E_{18}$ is not H, are provided. The corroles can be used for tumor detection and treatment, in photovoltaic devices, as catalysts and as intermediates.

25 Claims, No Drawings

METHOD FOR THE PREPARATION OF SELECTIVELY-SUBSTITUTED CORROLES AND NEW SUBSTITUTED CORROLES

FIELD OF THE INVENTION

The present invention relates to novel substituted corroles and to methods for their preparation.

BACKGROUND OF THE INVENTION

Corroles are tetrapyrrole macrocycles that are closely related to porphyrins, with one carbon atom less in the outer periphery and one NH proton more in their inner core. They may also be considered as the aromatic version (identical skeleton) of the only partially conjugated corrin, the cobalt-coordinating ligand in Vitamin $B_{12}$.

Porphyrins, phthalocyanines, and related macrocycles are extensively investigated in many applications, among them photodynamic therapy and catalysis. The most promising candidates for selective association to tumor cells are amphiphilic derivatives and chiral metal complexes are of prime importance for the utilization in asymmetric catalysis. Both structural types present a significant synthetic challenge because of the high symmetry of the most common precursors, tetraarylporphyrins and phthalocyanine. On the other hand, the less symmetric corroles could be very useful candidates for the above mentioned purposes. However, this potential was not explored until most recently because of the non-availability of simple synthetic methodologies for the preparation of corroles.

For decades, the chemistry of corroles was almost entirely limited to derivatives with fully alkylated β-pyrrole positions,[1] with only three examples of meso-only substituted corroles.[2] This situation changed dramatically recently with the disclosure by the present inventors (see WO 01/18771) of the first facile methodologies for the synthesis of 5,10,15-triarylcorroles from simple aldehydes and pyrrole:[3] about 80 new corroles that are substituted only at the three meso-carbon atoms were reported by now.[4] This development finally opened the gate for extensive investigations of corroles in the many applications that tetraarylporphyrins are constantly utilized.[5] Particularly, the metal complexes of 5,10,15-tris(pentafluorophenyl)corrole (1 in Scheme 1) were shown to be very efficient catalysts for atom (oxygen) and group (carbene, nitrene) transfer to organic substrates.[6] In fact, for the latter reactions the corrole metal complexes are significantly more efficient than analogous porphyrins.[6c, 6e] In addition, a water-soluble derivative of 1 (obtained by replacing its para-F atoms by pyridylium cations) was shown to be more efficient in inhibiting growth factors in tumor cells than analogous porphyrins and quite novel photophysical properties of non-transition metal corroles were recently disclosed.[7,8]

The two major structural peculiarities of corroles relative to porphyrins are the presence of three rather than two NH protons in the coordination core and the lower symmetry. Large emphasis was given to the first feature, particularly for stabilization of metal ions in high oxidation states,[9] while the other one was quite ignored. For example, although N-substituted corroles were reported as early as 1965,[10] the fact that these molecules are chiral was not appreciated until most recently.[11] A different aspect is the possibility of selective substitution of the macrocycle's protons, which could not be explored for the traditional corroles because they were fully alkylated at the β-pyrrole carbon atoms.[12] On the other hand, electrophilic substitution of porphyrins and phthalocyanines either proceeds to completion or provides an almost intractable mixture of products and isomers.[13] For example, even a bis-sulfonated phthalocyanine that was separated from mono- and multi-sulfonated products was shown to be a mixture of at least eight isomers.[14] In principle, the situation for meso-only substituted corroles could be better if the four different β-pyrrole carbon atoms display highly significant different reactivities. Otherwise, the number of possible products will be exceedingly large, up to 140 (see Scheme 1 herein).

SUMMARY OF THE INVENTION

The present invention relates to new corroles of formula I:

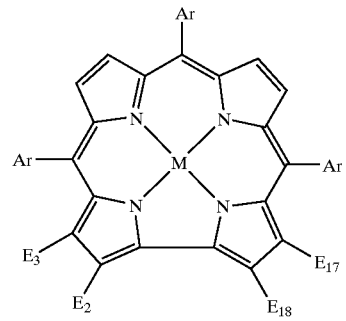

and to salts and optically active isomers thereof, wherein:
Ar is aryl or heteroaryl;
M is absent or is a metal selected from Al, Ga, Co, Mn, Fe, Ru, Sn, Cr or Rh;
$E_2$, $E_3$ and $E_{17}$, the same or different, each is H, $SO_2Cl$, $SO_3H$, $SO_2NR_1R_2$, $CO_2H$, $CO_2R$, COCl, $CONR_1R_2$, CHO or $NO_2$, R is alkyl or aryl and $R_1$ and $R_2$, the same or different, each is H, alkyl, aryl or together with the N atom to which they are attached form a saturated 5–6 membered ring optionally containing a further heteroatom selected from O, S and N; and
$E_{18}$ is H or CHO; or
$E_3$ is H and $E_2$ and $E_{17}$ are each $SO_2$, both $SO_2$ groups being linked by a bridge $R_3N(R_4)$-phenyl-$(R_4)NR_3$, wherein $R_3$ is H, alkyl, phenyl or aralkyl, and $R_4$ is alkylene; and
provided that at least one of $E_2$, $E_3$, $E_{17}$ and $E_{18}$ is not H.

The present invention also relates to new processes for selective substitution of corroles.

The corroles of the invention are useful for many purposes including, but not being limited to, catalysis of organic reactions, in photovoltaic cells, and for diagnosis and treatment of tumors or as intermediates.

DETAILED DESCRIPTION OF THE INVENTION

In the corroles of the formula I of the present invention, Ar in the positions 5, 10 and 15 may be aryl or heteroaryl. As used herein, the term "aryl" refers to a phenyl or naphthyl radical optionally substituted by one or more halogen atoms, or by one or more C1–C6 alkyl, C1–C6 alkoxy, nitro, hydroxy, amino, or pyridyl. Thus, Ar may, for example, be 2,6-dichlorophenyl, 2,6-difluorophenyl, pentafluorophenyl, 4-methoxy-2,3,5,6-tetrafluorophenyl, 4-(pyrid-2-yl)-2,3,5, 6-tetrafluorophenyl, and 4-(N-methyl-pyrid-2-ylium)-2,3,5, 6-tetrafluorophenyl. In one preferred embodiment, Ar is pentafluorophenyl.

As used herein, the term "heteroaryl" refers to a 5–6 membered heteroaromatic radical containing one or more heteroatoms selected from O, S and/or N such as, but not being limited to, pyrryl, furyl, thienyl, oxazolyl, thiazolyl, pyridyl, and pirazinyl.

As used herein, the term "alkyl" alone or as part of a radical such as "aralkyl" or "alkylene" refers to a straight or branched C1–C6 alkyl radical such as, but not limited to, methyl, ethyl, propyl, isopropyl, butyl, pentyl and hexyl.

In one embodiment of the invention, $E_2$ and $E_{17}$ are $SO_2Cl$ and $E_3$ and $E_{17}$ are hydrogen. These compounds are prepared by chlorosulfonation of the 5,10,15-tris(Ar)corrole with excellent selectivity as to produce the bis-functionalized corrole in high yield, as depicted in Scheme 2 herein. In one preferred embodiment, the 5,10,15-trispentafluorophenyl)corrole (compound 1 in Scheme 2) is reacted with chlorosulfonic acid thus obtaining 2,17-bis (chlorosulfonyl)-5,10,15-tris pentafluorophenyl)corrole (compound 2).

In another embodiment of the invention, $E_2$ and $E_{17}$ are $SO_3H$ and $E_3$ and $E_{17}$ are hydrogen. These compounds are prepared by hydrolysis of the corresponding 2,17-bis (chlorosulfonyl) derivatives. In one preferred embodiment, hydrolysis of compound 2 provided the bis-sulfonic acid derivative 3, 5,10,15-tris (pentafluorophenyl)corrole 2,17-bis(sulfonic acid), in which the clear separation of the hydrophilic residues from the lipophilic parts provides amphiphilicity, a highly desirable feature in many applications. Alternatively, the same compound 3 is prepared in one step via the reaction of compound 1 with 98% $H_2SO_4$ (in a ratio of 9:1 between 3 and 5,10,15-tris (pentafluorophenyl) corrole 3,17-bis(sulfonic acid, compound 12).

Chlorosulfonation presents two major advantages relative to direct sulfonation: milder reaction conditions and larger synthetic utility of the product ($RSO_2Cl$ vs. $RSO_3H$). On the other hand, the large reactivity of chlorosulfonic acid (CSA) presents a problem in reactants with multiple reactive sites: the preferred site for substitution reactions of tetraarylporphyrins with CSA are the aryls and the various available positions in phthalocyanines are substituted with very low selectivity.[15] In sharp contrast, the reaction of 1 with excess CSA displays very high selectivity for the 2,17-bis-substituted corrole (compound 2). The only other product (11,≦3%) was the 3,17-isomer, which was isolated after amidation of 2 by piperidine and subsequent metallation by cobalt (Scheme 2). Both the 3,17- and 2,17-regio-isomers were fully characterized by NMR spectroscopy and X-ray crystallography of their (triphenylphosphine)cobalt(III) complexes, 13 and 14, respectively.

In a further embodiment of the invention, $E_2$ and $E_{17}$ are $SO_2NR_1R_2$, and $E_3$ and $E_{17}$ are hydrogen. $R_1$ and $R_2$ may be H; C1–C6 straight or branched alkyl such as methyl, ethyl, propyl, isopropyl, butyl, isobutyl, pentyl, hexyl; aryl as defined herein above, or together with the N atom to which they are attached form a saturated 5–6 membered ring optionally containing a further heteroatom selected from O, S and N such as, but not limited to, pyrrolidino, piperidino, piperazino and morpholino. In one preferred embodiment, $NR_1R_2$ is a piperidino ring. These compounds can be prepared by reaction of the corresponding 2,17-bis (chlorosulfonyl) derivative with the amine $HNR_1R_2$. In one preferred embodiment, 2,17-bis(piperidinosulfonyl)-5,10, 15-tris (pentafluorophenyl)corrole (compound 4) is obtained by reaction of 2,17-bis (chlorosulfonyl)-5,10,15-tris (pentafluorophenyl)corrole (2) with piperidine.

In still another embodiment of the invention, $E_2$ and $E_{17}$ are linked by a sulfonamido bridge $SO_2N(R_3)$—$R_4$-phenyl-$R_4$—$N(R_3)SO_2$, wherein $R_3$ is H, alkyl, phenyl or aralkyl, wherein alkyl is as defined above, and $R_4$ is C1–C4 alkylene, preferably methylene. In one embodiment, the diamine $N(R_3)$—$R_4$-phenyl-$R_4$—$N(R_3)$ is 1,4-di (isopropylaminomethyl)benzene ($R_3$ is isopropyl and $R_4$ is —$CH_2$—); in another embodiment, the diamine is non-racemic 1,4-di[(-)phenetylaminomethyl] benzene ($R_3$ is phenethyl and $R_4$ is —$CH_2$—). These compounds are prepared by a process which comprises reacting the corresponding 2,17-bis(chlorosulfonyl) derivative with the bisamine 4-di(isopropylaminomethyl)benzene or non-racemic 1,4-di ((-)phenethylaminomethyl)benzene, respectively.

In yet another embodiment, the present invention relates to a mononitro derivative of formula I wherein $E_3$ is $NO_2$, to a dinitro derivative wherein $E_3$ and $E_{17}$ are $NO_2$, and to a trinitro derivative wherein $E_2$, $E_3$ and $E_{17}$ are $NO_2$. These compounds can be prepared by selective nitration of the 5,10,15-tris(Ar)corrole of formula I as shown in Scheme 3 for the gallium complex.

Selective nitration of the gallium complex of 5,10,15-tris (pentafluorophenyl)-corrole 5 can be carried out in the presence of 0.7–2 equivalents of an oxidant, whereby in the presence of <0.7 equivalents of oxidant, the gallium complex of 3-nitro-5,10,15-tris(pentafluorophenyl)corrole 6 is obtained, and in the presence of 2 equivalents of oxidant, the gallium complex of 3,17-dinitro-5,10,15-tris (pentafluorophenyl)corrole 7 is obtained along with a small amount of 2,3,17-trinitro-5,10,15-tris(pentafluorophenyl) corrole 8. Using between 0.7 to 2.0 equivalents of oxidant, different percentages of the three products are obtained. The oxidant used should be strong enough to convert $NO_2^-$ to $NO_2$ and is, for example, tris(4-bromophenyl)aminium hexachloroantimonate In yet a further embodiment, the present invention relates to a monoformyl derivative of formula I wherein $E_3$ is CHO, and to a diformyl derivative wherein $E_3$ and $E_{17}$ are CHO. These compounds can be prepared by selective formylation of the 5,10,15-tris(Ar)corrole of formula I as shown in Scheme 4 for the gallium complex. Thus, selective formylation of the gallium complex of 5,10,15-tris (pentafluorophenyl)corrole (5) is carried out in the presence of 1–100 equivalents of Vilsmeier reagent ($POCl_3$ and DMF) followed by hydrolysis, whereby in the presence of 1 equivalent of reagent, the gallium complex of 3-formyl-5, 10,15-tris (pentafluorophenyl)corrole 9 is obtained, and in the presence of excess reagent, the gallium complex of 2,3,17-triformyl-5,10,15-trispentafluorophenyl)corrole 10 is obtained. According to the same procedure, selective formylation of the aluminium complex of 5,10,15-tris (pentafluorophenyl)corrole provides the compounds 23 and 24 (as main product); with the cobalt complex, the compounds 25 and 26 (as main product) are obtained; and with the Mn complex, the compounds 27 and 28 (as main product) are obtained.

In still an additional embodiment, compounds of formula I are provided wherein $E_3$ is COCl, COOH or COOR wherein R is alkyl or aryl. These compounds are prepared by reaction of the 5,10,15-tris(Ar)-corrole with phosgene and further hydrolysis and, if desired, reaction with the desired alcohol or phenol ROH to produce the ester.

In still yet another embodiment, the invention relates to metal complexes of the compounds of formula I, wherein the metal is Al, Ga, Co, Mn, Fe, Ru, Sn, Cr or Rh. Gallium(III), chromium(III), manganese(III), cobalt(III), tin(IV) and rhodium can be inserted in the inner core of 3, using the methods that were developed for metal insertion into 1.[6,8,16]

Generally, the same methods that were developed for metallation of corrole 1 worked for the metallation of the sulfonated derivative 3 as well: Co(OAc)$_2$/PPh$_3$/EtOH for obtaining the (triphenylphosphine)cobalt(III) complex 17; CrCl$_2$/pyridine for the (pyridine)$_2$chromium(III) complex 19; Mn(OAc)$_2$/DMF for the manganese(III) complex 16; SnCl$_2$·2H$_2$O/DMF for the (chloro)tin(M) complex 18; and GaCl$_3$/pyridine for the gallium(III) complex 15. For the preparation of the triphenylphosphine Co(III) and Rh(III) complexes 13 and 14, or 30, compound 4 is reacted with Co(OAc)$_2$ or [Rh(CO)$_2$Cl$_2$, respectively, followed by addition of triphenylphosphine.

In order to obtain compounds of formula I wherein $E_2$, $E_3$ and $E_{17}$ are not the same, one substituent can be inserted first, e.g. the CHO group at $E_3$ by reaction with the Vilsmeier reagent, and then introducing another substituent, e.g. SO$_2$Cl at $E_{17}$ by chlorosulfonation.

Initially, all three reactions—chlorosulfonation, formylation and nitration were attempted on the metal-free corrole 1. Chlorosulfonation proceeded very well, but the results with formylation and nitration were less satisfactory and, therefore, the two latter reactions were performed on the gallium(III) complex of 1 (compound 5).

The nitration of 5 was performed by its mixing with a suspension of NaNO$_2$ in CH$_3$CN (no reaction) and at-once addition of a limited amount of the one-electron oxidant tris(4-bromophenyl)aminium hexachloroantimonate (CAS No. 24964-91-8). With 75 mol % oxidant, the major product was the mononitro corrole 6 (isolated yield: 84%), with 200 mol % the bis-nitro complex 7 was isolated in 94% yield, and with 300 mol % of the oxidant, the trinitrocorrole 8 and 7 were isolated in 27 and 58%, respectively (Scheme 3). Most important, all three products were obtained as single isomers, i.e., only one out of four possible mono-, one out of sixteen bis-, and one out of twenty eight tris-nitro corroles. This was elucidated by NMR spectroscopy and further substantiated by X-ray crystallography of all three nitro-substituted corroles.

For the synthesis of the mono-substituted corrole by formylation, a limited amount of the Vilsmeier reagent was used and the desired product 9 was obtained in 87% yield as a single isomer, accompanied by a small amount of the bis-substituted product 10. On the other hand, the reaction does not proceed further than bis-substitution even with a 100-fold excess of reagent and 10 can be isolated in 64% yield without any indication for other isomers. Based on a spectral comparison with the nitro-substituted products, the substitution patterns are identical for the mono-nitro and the mono-formyl corroles, but different for the bis-substituted products.

The chlorosulfonation reaction was only performed with excess reagent, which served as solvent as well. Only bis-substituted products were obtained, in a ratio of 96:4 in favor of the 2,17-relative to the 3,17-substituted isomer. Upon hydrolysis, the bis-sulfonate corrole 3 was obtained in 71% relative to 1.

Metallation of compound 3 was carried out by insertion of gallium(III), chromium(III), manganese(III), cobalt(III), and tin(IV) in the inner core of 3, using the methods that were developed for metal insertion into 1.[6,8,16] In all cases, the reactions proceeded quantitatively and the products were identified via comparison to the corresponding metal complexes of 1.

Metallation of compound 1 was carried out by insertion of aluminium(III), cobalt(III), and manganese(III) by the published methods,[6,8,16] and the metallated compounds were further formylated.

Thus, according to the present invention, it is shown that despite the 139 possible products that can be obtained by substitution of the 5,10,15-tris(pentafluorophenyl)corrole 1 (see Scheme 1), according to the present invention novel corrole derivatives can be prepared by facile and highly selective electrophilic substitution by: (i) chlorosulfonation of corrole 1 to 2, followed either by hydrolysis for the preparation of the amphiphilic corroles 3 and 12 or by amidation and metal insertion for the preparation of chiral complexes; (ii) direct sulfonation of corrole 1 with sulfuric acid for preparation of the amphiphilic corroles 3 and 12; (iii) nitration of metallated corrole 1 for preparation of the corroles 6–8; (iv) formulation of metallated corrole 1 for preparation of the corroles 9–10; (v) chlorocarbonylation of metallated corrole 1 for preparation of the corrole 21 followed by hydrolysis to obtain the corrole 22. This shows the feasibility of electrophilic substitution of corroles as a synthetic tool to many novel derivatives.

The novel compounds of the invention are useful in several applications. For example, some of the compounds of formula I such as those bearing a sulfonic or carboxylic group, bind to proteins and interact with cells, and can be used for tumor detection by fluorescence techniques or for treatment of tumors by killing cells via catalysis, in the presence or absence of light. For example, compound 3 and its non-transition and transition metal complexes and compounds 22 and 31 (relying on their activation of oxygen and/or oxygen-containing molecules), can be used for treatment of tumors by photodynamic therapy (PDT) in combination with light; the compounds 3, 12 and the Ga-5 complexes 15 and 22 are useful for tumor detection by fluorescence techniques; and the Mn-5 complex 16 is useful for treatment of tumors in absence of light.

Thus, the present invention further provides a pharmaceutical composition comprising a pharmaceutically acceptable carrier and a corrole of formula 1 selected from the compounds:

5,10,15-tris(pentafluorophenyl)corrole-2,17-bis(sulfonic acid)

5,10,15-tris(pentafluorophenyl)corrole-3,17-bis(sulfonic acid)

5,10,15-Tris(pentafluorophenyl)-2,17-bis(sulfonic acid) corrolato gallium(III) (pyridine)

5,10,15-Tris(pentafluorophenyl)-2,17-bis(sulfonic acid)-corrolato manganese(III)

5,10,15-Tris(pentafluorophenyl)-2,17-bis(sulfonic acid)-corrolato cobalt(III) (triphenylphosphine)

5,10,15-Tris(pentafluorophenyl)-2,17-bis(sulfonic acid)-corrolato chromium(III) (pyridine)$_2$ 5,10,15-Tris(pentafluorophenyl)-2,17-bis(sulfonic acid)-corrolato iron(III)

5,10,15-Tris(pentafluorophenyl)corrolato gallium(III) (pyridine) 3-carboxylic acid; and 5,10,15-Tris(pentafluorophenyl)corrolato gallium(II) (pyridine) 3-carboxylic acid methyl ester.

In one embodiment, the pharmaceutical composition is for treatment of tumors in combination with light (PDT), wherein the corrole is selected from:

5,10,15-tris(pentafluorophenyl)corrole-2,17-bis(sulfonic acid)

5,10,15-tris(pentafluorophenyl)corrole-3,17-bis(sulfonic acid)

5,10,15-Tris(pentafluorophenyl)-2,17-bis(sulfonic acid) corrolato gallium(III) (pyridine)

5,10,15-Tris(pentafluorophenyl)-3,17-bis(sulfonic acid)-corrolato manganese(III)

5,10,15-Tris(pentafluorophenyl)-2,17-bis(sulfonic acid)-corrolato cobalt(III) (triphenylphosphine)

5,10,15-Tris(pentafluorophenyl)-2,17-bis(sulfonic acid)-corrolato chromium(III) pyridine)$_2$ 5,10,15-Tris(pentafluorophenyl)-2,17-bis(sulfonic acid)-corrolato iron(III)

5,10,15-Trispentafluorophenyl)corrolato gallium(III) (pyridine) 3-carboxylic acid; and 5,10,15-Tris(pentafluorophenyl)corrolato gallium(III) (pyridine) 3-carboxylic acid methyl ester.

In another embodiment, the pharmaceutical composition is for treatment of tumors in the absence of light, wherein the corrole is selected from:

5,10,15-Tris(pentafluorophenyl)-2,17-bis(sulfonic acid) corrolato gallium(III) (pyridine); and 5,10,15-Tris(pentafluorophenyl)-2,17-bis(sulfonic acid)-corrolato manganese(III)

In a further embodiment, the pharmaceutical composition is for tumor detection by fluorescence techniques, wherein the corrole is selected from:

5,10,15-tris(pentafluorophenyl)corrole-2,17-bis(sulfonic acid)

5,10,15-tris(pentafluorophenyl)corrole-3,17-bis(sulfonic acid)

5,10,15-Tris(pentafluorophenyl)-2,17-bis(sulfonic acid) corrolato gallium(III) (pyridine)

5,10,15-Tris(pentafluorophenyl)corrolato gallium(III) (pyridine) 3-carboxylic acid; and 5,10,15-Tris(pentafluorophenyl)corrolato gallium(III) (pyridine) 3-carboxylic acid methyl ester.

Other corroles of the invention are intermediates for compounds that can be used for tumor detection or treatment such as the compounds substituted by COCl or SO$_2$Cl. The nitrated and formylated derivatives must first be made charged via reduction of the nitro to amine and quaternization to (corrole)(—NR$_3^+$)x and the formylated via oxidation to (corrole)(—CO$_2^-$)x.

The corroles of the present invention are formulated into final pharmaceutical compositions for administration to the patient or applied to an in vitro target using techniques well-known in the art, for example, as summarized in Remington's Pharmaceutical Sciences, Mack Publishing Co., Easton, Pa., latest edition. The compositions can be administered systemically, in particular by injection, or can be used topically.

For diagnosis, the corrole derivatives may be used alone or may be labeled with a radioisotope or other detecting means as known in the art.

The amount of corrole derivative to be administered will be according to the experience accumulated in PDT techniques using porphyrins derivatives, and will vary depending on the choice of the derivative used as active ingredient, the condition to be treated, the mode of administration, the age and condition of the patient, and the judgement of the physician.

The wavelenght of irradiating light is preferably chosen to match the maximum absorbance of the corrole derivative. The suitable wavelenght for any of the compounds can readily be determined from its absorption spectrum.

In addition to in vivo use, the corrole derivatives of the invention may be useful in the treatment of materials in vitro to kill harmful viruses or infectious agents, such as harmful bacteria. For example, blood and blood plasma to be used for future transfusion can be treated with a compound of the invention and irradiated to effect sterilization.

Another application of the compounds of the invention is in photovoltaic cells, through binding to semiconductors and conversion of light into electricity; preferred compounds for this application are metal complexes such as Ga-5 and Mn-5 complexes of the compound 3, bound to semi-conductors such as titanium and tin oxides.

A further application of the compounds of the invention is in asymmetric catalysis, for example, utilizing the metal complexes, e.g. Rh-3 complexes and analogous compounds, with different amines or alcohols (either racemic, relying on the metal-chirality, or non-racemic), for enantioselective epoxidation, hydroxylation, cyclopropanation, aziridination, and other related processes.

The invention will now be illustrated by the following non-limiting Examples.

EXAMPLES

In the Examples, the following compounds 1–32 will be identified by their numbers in bold:

1. 5,10,15-Tris(pentafluorophenyl)corrole ("tpfc")
2. 2,17-Bis(chlorosulfonyl)-5,10,15-tris(pentafluorophenyl) corrole
3. 5,10,15-Tris(pentafluorophenyl)-2,17-bis(sulfonic acid)-corrole
4. 2,17-Bis piperidinosulfonyl)-5,10,15-tris (pentafluorophenyl)corrole
5. 5,10,15-Tris(pentafluorophenyl)corrolato gallium(III) (pyridine)
6. 3-Nitro-5,10,15-tris(pentafluorophenyl)corrolato gallium (III)(pyridine)$_2$
7. 3,17-Dinitro-5,10,15-tris(pentafluorophenyl)corrolato gallium(III)(pyridine)$_2$
8. 3,17,18-Trinitro-5,10,15-tris(pentafluorophenyl)corrolato gallium(III)(pyridine)$_2$
9. 3-Formyl-5,10,15-tris(pentafluorophenyl)corrolato gallium(III)(pyridine)
10. 2,17-Bis(formyl)-5,10,15-tris(pentafluorophenyl) corrolato gallium(III)(pyridine)
11. 3,17-Bis(chlorosulfonyl)-5,10,15-tris (pentafluorophenyl)corrole
12. 5,10,15-Tris(pentafluorophenyl)-3,17-bis(sulfonic acid)-corrole
13. 2,17-Bis(piperidinosulfonyl)-5,10,15-tris (pentafluorophenyl)corrolato cobalt(III) (triphenylphosphine)
14. 3,17-bis(piperidinosulfonyl)-5,10,15-tris (pentafluorophenyl)corrolato cobalt(III) (triphenylphosphine)
15. 5,10,15-Trispentafluorophenyl)-2,17-bis(sulfonic acid) corrolato gallium(III) (pyridine)
16. 5,10,15-Tris(pentafluorophenyl)-2,17-bis(sulfonic acid)-corrolato manganese(III)
17. 5,10,15-Tris(pentafluorophenyl)-2,17-bis(sulfonic acid)-corrolato cobalt(III) (triphenylphosphine)
18. 5,10,15-Tris(pentafluorophenyl)-2,17-bis(sulfonic acid)-corrolato tin(IV) (chloride)
19. 5,10,15-Tris(pentafluorophenyl)-2,17-bis(sulfonic acid)-corrolato chromium(III) (pyridine)$_2$
20. 5,10,15-Tris(pentafluorophenyl)-2,17-bis(sulfonic acid)-corrolato iron(III)
21. 3-chlorocarbonyl-5,10,15-tris(pentafluorophenyl) corrolato gallium(III)(pyridine)
22. 5,10,15-Tris(pentafluorophenyl)corrolato gallium(III) (pyridine) 3-carboxylic acid
23. 3-Formyl-5,10,15-tris(pentafluorophenyl)corrolato aluminum(III)(pyridine)$_2$
24. 2,17-Bis(formyl)-5,10,15-tris(pentafluorophenyl) corrolato aluminum(III) (pyridine)$_2$
25. 2,17-Bis(formyl)-5,10,15-tris(pentafluorophenyl) corrolato cobalt (III)(pyridine)$_2$
26. 2,3,17-Tris(formyl)-5,10,15-tris(pentafluorophenyl) corrolato cobalt(III)(pyridine)$_2$ 27. 3-Formyl-5,10,15-tris(pentafluorophenyl)corrolato manganese(III)(pyridine)
28. 2,17-Bis(formyl)-5,10,15-tris(pentafluorophenyl) corrolato manganese(III) (pyridine)
29. 3,17-Bis(piperidinosulfonyl)-5,10,15-tris (pentafluorophenyl)corrole
30. 2,17-Bis(piperidinosulfonyl)-5,10,15-tris (pentafluorophenyl)corrolato rhodium (III) (triphenylphosphine)
31. 5,10,15-Tris(pentafluorophenyl)corrolato gallium(III) (pyridine) 3-carboxylic acid methyl ester
32. 3-nitro-5,10,15-tris(pentafluorophenyl)corrolato tin(IV) (chloride)

Experimental

Physical methods: The NMR spectra were recorded on a Bruker AM200 spectrometer, operating at 200 MHz for $^1$H and 188 MHz for $^{19}$F. Chemical shifts in the $^1$H NMR spectra are reported in ppm relative to residual hydrogens in the deuterated solvent: $\delta$=7.20 and 7.24 for benzene and chloroform, respectively, and to CFCl$_3$ ($\delta$=0.00) in the $^{19}$F NMR spectra. Coupling constants J are reported in Hz. A HP 8452A diode array Spectrophotometer was used to record the electronic spectra. Mass spectroscopy was performed on a Finnigan TSQ 70 instrument with isobutane as carrier gas. The diffraction measurements were carried out on a Nonius Kappa CCD diffractometer, using graphite monochromated MoK$\alpha$ radiation ($\lambda$=0.7107 Å).

Materials: All reagents were purchased from commercial sources and used as received unless otherwise noted. Acetonitrile was dried over P$_2$O$_5$ and distilled.

Synthetic methods: The synthetic details for the preparation of 5,10,15-tris(pentafluorophenyl)corrole (H$_3$(tpfc), (compound 1) and 5,10,15-tris (pentafluorophenyl)corrolato gallium(III)(pyridine) (Ga(tpfc)(pyr), (compound 4) are provided in previous publications.[3,8]

Example 1

Preparation of Compound 2

Compound 2 was prepared by chlorosulfonation of compound 1. Thus, 80 mg of compound 1 (100 μmol) and 2 mL of chlorosulfonic acid (30 mmol) were stirred at 25° C. for 5 min, after which the reaction mixture was cooled by an ice bath and treated with small ice chips (5–10 g, caution!). The product was obtained via the addition of 20 mL distilled water and CH$_2$Cl$_2$ (the CH$_2$Cl$_2$ solution was washed 3 times with distilled water) and evaporation. Based on NMR spectroscopy, 2 was obtained in quantitative yield.

2: $^1$H NMR (200 MHz, CDCl$_3$) $\delta$=9.44 (s, 1H), 8.95 (s, 1H), 8.60 (d, J=5.0 Hz, 1H), 8.50 (d, J=5.0 Hz, 1H), 8.41 (d, J=5.0 Hz, 1H), 8.18 (d, J=5.0 Hz, 1H); $^{19}$F NMR (188 MHz, CDCl$_3$) $\delta$=−137.5 (d, J=21.1 Hz, 4F), −138.3 (d, J=18.1 Hz, 2F), −149.6 (t, J=21.31, 1F), −150.1 (t, J=21.21, 2F), −160.0 (m, 4F), −161.6 (m, 2F); MS (DCI$^-$): m/z (%): 991.8 (5) [M$^-$], 892 (20) [M$^-$−SO$_2$Cl].

Example 2

Preparation of Compound 3

Compound 3 was prepared either by hydrolysis of compound 2 (procedure 2a) or by direct sulfonation of compound 1 (procedure 2b).

2a Hydrolysis of compound 2: A suspension of 2 in 20 mL water was refluxed for 12 hr. The solution was filtered and evaporated to dryness as to provide 3 in 71% yield based on 1 (68 mg, 71 μmol).

3: $^1$H NMR (CD$_3$OD) $\delta$=9.68 (br. s, 1H), 9.14 (d, J=4.8 Hz, 1H), 8.98 (d, J=4.8 Hz, 1H), 8.90 (br. s, 1H), 8.86 (d, J=4.8 Hz, 1H), 8.84 (d, J=4.8 Hz, 1H); $^{19}$F NMR (188 MHz, CD$_3$OD) $\delta$=−137.5 (d, J=20.3 Hz, 2F), −137.8 (d, J=19.6 Hz, 4F), −149.8 (t, J=20.3, 1F), −150.8 (t, J=20.1, 1F), −152.1 (t, J=19.4, 1F), −160.3 (m, 2F), −160.8 (m, 2F), −163.1 (m, 2F); UV/Vis (buffer solution, pH 7.00): $\lambda_{max}$ ($\epsilon$(M$^{-1}$ cm$^{-1}$))=414 (71000), 430 (62000), 588 (15000), 620 (27000). MS (MALDI-TOF): m/z: 956.6 [M$^+$].

2b Direct sulfonation of compound 1: Sulfonation was carried out by adding concentrated sulfuric acid (98%, 1 mL) to solid 1 (35 mg) at room temperature and stirring the bright green solution (the protonated form of the corrole) for 1 h. The product was isolated by addition of ice cubes, neutralization by sodium carbonate, and separation from sodium sulfate via two cycles of adding ethanol, filtration and solvent evaporation. The quantitatively-formed product was examined by NMR (both CD$_3$OD and D$_2$O), which revealed the formation of compounds 3 and 12 in a ratio of 9/1.

Example 3

Preparation of Compound 4

Compound 4 was prepared by reaction of compound 2 and piperidine. Thus, a solution of 2 and piperidine (8 eq.) in CH$_2$Cl$_2$ (20 ml) was stirred for 30 min. The solution was washed twice by a solution of HCl (2M) and then by distilled water. The solvent was evaporated and 4 was obtained in quantitative yield.

4: $^1$H NMR (200 MHz, CDCl$_3$) $\delta$=9.50 (s, 1H), 8.83 (s, 1H), 8.64 (d, J=4.9 Hz, 1H), 8.58 (d, J=4.9 Hz, 1H), 8.47 (d, J=4.9 Hz, 1H), 8.32 (d, J=4.9 Hz, 1H), 3.27 (m, 8H), 1.5–2.0 (m, 12H); $^{19}$F NMR (188 MHz, CDCl$_3$) $\delta$=−137.5 (d, J=21.1 Hz, 4F), −138.3 (d, J=18.1 Hz, 2F), −149.6 (t, J=21.3 Hz, 1F), −150.1 (t, J=21.0 Hz, 2F), −160.0 (m, 4F), −161.6 (m, 2F); MS (DCI$^-$): m/z (%): 1090.1 (100) [M]$^-$ When piperidine was substituted by either 1,4-di (isopropylaminomethyl)benzene or non-racemic 1,4-di((−) phenetylaminomethyl)benzene, the corresponding sulfonamido-bridged corroles were obtained.

Example 4

Preparation of Compounds 13, 14 and 30

4a Preparation of Compounds 13 and 14

Compounds 13 and 14 were prepared by amidation of compound 2 with piperidine according to Example 3 above, insertion of cobalt in compound 4 by treatment with cobalt (II) acetate and further reaction with triphenylphosphine.

Thus, a solution of 4 and Co(OAc)$_2$.4H$_2$O (4 eq.) in pyridine (10 ml) was refluxed for 1 hr. The solvent was evaporated and the residue was dissolved in 10 ml CH$_2$Cl$_2$. At this stage, PPh$_3$ (4 eq.) was added and the residue was passed through a column of silica with CH$_2$Cl$_2$ as eluent. After recrystallization from benzene/heptane, compound 13 was obtained in 72% yield based on 1 (102 mg, 72 μmol). X-ray quality crystals of 13 were obtained by slow recrystallization from a mixture of benzene/heptane.

13: $^1$H NMR (200 MHz, benzene-d$_6$) $\delta$=9.64 (s, 1H), 8.68 (s, 1H), 8.37 (d, J=5.0 Hz, 1H), 8.24 (d, J=5.0 Hz, 1H), 8.14 (t, J=4.7 Hz, 2H), 6.64 (dt, J$^1$=2.4 Hz, J$^2$=7.5 Hz, 3H), 6.46 (dt, J$^1$=2.8 Hz, J$^2$=7.4 Hz, 6H), 4.71 (dd, J$^1$=7.5 Hz, J$^2$=11.7 Hz, 6H), 3.51 (t, J=5.0 Hz, 4H), 3.1 (m, 4H), 1.46 (m, 4H), 1.27 (m, 2H), 1.01 (m, 4H), 0.63 (m, 2H); $^{19}$F NMR (188 MHz, benzene-d$_6$) $\delta$=−137.0 (dd, J$^1$=24.5 Hz, J$^2$=6.8 Hz, 1F), −137.4 (dd, J$^1$=17.9 Hz, J$^2$=6.8 Hz, 1F), −137.9 (m, 2F), −138.6 (dd, $J^1$=28.8 Hz, $J^2$=6.8 Hz, 1F), −139.5 (dd, $J^1$=24.5 Hz, $J^2$=6.8 Hz, 1F), −151.0 (t, J=21.5, 1F), −152.2 (t, J=21.5, 1F), −154.1 (t, J=21.5, 1F), −161.0 (m, 4F), −164.2 (m, 2F); UV/Vis (CH$_2$Cl$_2$): $\lambda_{max}$ ($\epsilon$(M$^{-1}$ cm$^{-1}$))=314 (20000), 382 (43000), 410 (44000), 564 (16000), 606 (15000); MS (DCI$^-$): m/z (%): 1145.8 (4) [M−PPh$_3$]$^-$, 999 (100) [M−PPh$_3$, −SO$_2$NC$_5$H$_{10}$]$^-$.

Careful chromatographic treatment of the recrystallization solution of the 2,17-substituted isomer 13 allowed the isolation of another minor product (3% yield), that was identified as the 3,17-substituted isomer 14. X-ray quality crystals of complex 14 were obtained from benzene/heptane".

14. $^1$H NMR (200 MHz, benzene-d$_6$) δ=9.05 (s, 2H), 8.34 (d, J=4.9 Hz, 2H), 8.20 (d, J=4.9 Hz, 2H), 6.61 (dt, $J^1$=2.3 Hz, $J^2$=7.5 Hz, 3H), 6.40 (dt, $J^1$=2.7 Hz, $J^2$=7.9 Hz, 6H), 4.71 (dd, $J^1$=7.5 Hz, $J^2$=11.7 Hz, 6H), 3.17 (m, 8H), 1.28 (m, 8H), 1.08 (m, 4H); $^{19}$F NMR (188 MHz, benzene-d$_6$) δ=−136.7 (d, J=24.7 Hz, 2F), −137.2 (d, J=25.0 Hz, 2F), δ−137.7 (d, J=21.8 Hz, 1F), −139.7 (d, J=23.4 Hz, 1F), −152.2 (t, J=21.7, 1F), −154.3 (t, J=21.3, 2F), −161.3 (m, 4F), −164.2 (m, 2F).

4b Preparation of Compound 30

When Co was substituted by Rh, rhodium complexes were obtained in high yield. Thus, compound 4 (60 mg, 0.055 mmol) was dissolved in dry toluene (50 mL) under N$_2$, and dry K$_2$CO$_3$ (0.63 g, 4.6 mmol), [{Rh(CO)$_2$Cl}$_2$] (90 mg, 0.23 mmol), and PPh$_3$ (0.12 mg, 0.46 mmol) were added to this mixture. The mixture was heated to reflux for 1 hr under N$_2$. The reaction mixture was cooled to room temperature, filtered, and the solvent was evaporated. The residue was passed through a column of silica with CH$_2$Cl$_2$ as eluent at the beginning and then with ethyl acetate. The fraction that was separated by ethyl acetate was then chromatographed with dichloromethane/hexane/THF/ethylacetate (70:130:2:1) on a silica preparative thin layer, and the main fraction was collected. After recrystallization from hexane/CH$_2$Cl$_2$, compound 30, the triphenylphosphine Rh complex of 4 (45.5 mg, 0.031 mmol) was obtained in 57% yield.

30: $^1$H NMR (200 MHz, CDCl$_3$) δ=9.28 (s, 1H), 8.32 (d, J=4.9 Hz, 1H), 8.2 (m, 3H), 8.08 (d, J=4.9 Hz, 1H), 7.08 (t, J=8.0 Hz, 3H), 6.77 (m, 6H), 4.64 (dd, $J^1$=7.9 Hz, $J^2$=12.4 Hz, 6H), 2.8–3.4 (m, 8H), 1.0–1.8 (m, 12H); $^{19}$F NMR (188 MHz, CDCl$_3$) δ=−137.3 (m, 4F), −138.1 (d, J=25.4 Hz, 1F), −138.5 (d, J=23.6 Hz, 1F), −152.4 (t, J=20.5, 1F), −152.9 (t, J=20.5, 1F), −154.1 (t, J=20.5, 1F), −161.8 (m, 4F), −164.4 (m, 2F); UV/Vis (CH$_2$Cl$_2$): $\lambda_{max}$=410 (Soret), 594 (Q-band); MS (DCI$^+$): m/z (%): 1452.5 [MH]$^+$.

Example 5

Metallation of Compound 3

The most variable compounds of the invention are 2 and 3, because of the easy substitution of the chloride in the —SO$_2$Cl functions of 2 and the large variety of metal ions that can be inserted into either 2 or 3. In the present example, metallation of compound 3 is described. Generally, the same methods that were developed for corrole 1 worked for 3 as well: GaCl$_3$/pyridine for obtaining compound 15, the gallium(III) complex of 3; Mn(OAc)$_2$/DMF for obtaining compound 16, the manganese(III) complex of 3; Co(OAc)$_2$/PPh$_3$/EtOH for obtaining compound 17, the (triphenylphosphine)cobalt(III) complex of 3; SnCl$_2$.2H$_2$O/DMF for obtaining compound 18, the (chloro)tin(IV) complex of 3; and CrCl$_2$/pyridine for obtaining compound 19, the (bis-pyridine)chromium(III) complex of 3. Both compound 3 and its metal complexes were soluble in water and at the low concentrations that are relevant for UV-vis measurements (10$^{-4}$–10$^{-6}$ M), the linear plots obtained for elucidating the $\epsilon$ values indicate the absence of aggregation.

Metal complexes of compound 3 were prepared as follows:

5.1 Insertion of gallium(III): A solution of 3 (20 mg, 21 μmol) in pyridine (10 mL) was added to a flask that contains a large excess (about 0.2 g) of flame-dried GaCl$_3$ and the reaction mixture was heated to reflux for 30 min under argon, followed by evaporation of the solvent. The inorganic salts were separated by column chromatography on silica (eluent: MeOH:pyridine=20:1), affording 21 mg (19 μmol, 90% yield) of compound 15, the (pyridine)gallium(III) complex of 3.

15: $^1$H NMR (CD$_3$OD): δ=9.77 (s, 1H), 8.77 (s, 1H), 8.70 (d, $^3$J(H,H)=4.8 Hz, 1H), 8.57 (d, $^3$J(H,H)=4.8 Hz, 1H), 8.48 (t, $^3$J(H,H)=4.3 Hz, 2H), 8.27 (br. s, 2H), 7.71 (t, 1H), 7.30 (br. s, 2H); $^{19}$F NMR (CD$_3$OD): δ=−135.2 (d, $^3$J(F,F)=23.0 Hz,2F), −136.8 (d, $^3$J(F,F)=23.5 Hz, 4F), −153.5 (t, $^3$J(F,F)= 20.1 Hz, 1F), −154.1 (t, $^3$J(F,F)=20.5 Hz, 1F), −156.2 (t, $^3$J(F,F)=20.3 Hz, 1FF), −162.2 (m, 4F), −165.1 (m, 2F); UV/Vis (buffer solution, pH 7.30): $\lambda_{max}$ 424 nm ($\epsilon$ 75000), 588 (13600), 610 (17300); MS (MALDI-TOF): m/z: 1022.17 [M$^+$−pyridine].

5.2 Insertion of manganese(III): A flask loaded with a 10 mL DMF solution of 3 (15 mg, 16 μmol) and Mn(OAc)$_2$.4H$_2$O (15 mg, 61 μmol) was heated to reflux for 15 min, followed by evaporation of the solvent. The inorganic salts were separated by column chromatography on silica (eluent: EtOH), affording 15 mg (15 μmol, 94% yield) of compound 16, the manganese(III) complex of 3.

16: UV/Vis (buffer solution, pH 7.30): $\lambda_{max}$ 392 nm ($\epsilon$ 19000), 422 (21000), 480 (17000), 644 (11500), 610 (9500), 576 (9000); MS (MALDI-TOF): m/z: 1007.85 [M$^+$].

5.3 Insertion of cobalt(III): A 10 mL EtOH solution of 3 (10 mg, 10 μmol) and NaOAc (30 mg, 0.37 mmol) was mixed for 5 min at 25° C., after which PPh$_3$ (20 mg, 76 μmol) and Co(OAc)$_2$.4H$_2$O (20 mg, 80 μmol) were added and solution was mixed for another 30 min. Following solvent evaporation, column chromatography on silica with CH$_2$Cl$_2$ as eluent was used to remove the excess of PPh$_3$ and EtOH to free the product from inorganic salts, as to afford 12 mg (9 μmol, 90% yield) of compound 17, the (triphenylphosphine)cobalt(III) complex of 3.

17: $^1$H NMR (CD$_3$OD): δ=9.40 (s, 1H), 8.40 (m, 5H), 7.05 (t, $^3$J(H,H)=8.0 Hz, 3H), 6.70 (t, $^3$J(H,H)=7.7 Hz, 6H), 4.60 (dd, $^3$J(H,H)=7.8 Hz, $^3$J(P,H)=11.3 Hz, 6H); $^{19}$F NMR (CD$_3$OD): δ=−134.9 (dd, $^3$J(F,F)=24.0 Hz, $^4$J(F,F)=7.0 Hz, 1F), −135.2 (dd, $^3$J(F,F)=24.0 Hz, $^4$J(F,F)=7.0 Hz, 1F), −135.7 (dd, $^3$J(F,F)=24.0 Hz, $^4$J(F,F)=7.0 Hz, 1F), −136.7 (dd, $^3$J(F,F)=24.0 Hz, $^4$J(F,F)=7.0 Hz, 1F), −137.0 (m, 2F), −152.7 (t, $^3$J(F,F)=20.0 Hz, 1F), −153.0 (t, $^3$J(F,F)=20.0 Hz, 1F), −155.5 (t, $^3$J(F,F)=20.0 Hz, 1F), −161.4 (m, 4F), −164.7 (m, 2F); UV/Vis (MeOH): $\lambda_{max}$ ($\epsilon$): 378 nm (32000), 410 (33000), 558 (8600), 594 (9000);

5.4 Insertion of Tin(IV): A 10 mL DMF solution of 3 (12 mg, 13 μmol) and SnCl$_2$.2H$_2$O (12 mg, 53 μmol) was heated to reflux for 30 min, followed by evaporation of the solvent. Addition of CH$_2$Cl$_2$ to the residue, filtration, and solvent evaporation afforded 13 mg (12 μmol, 92% yield) of compound 18, the (chloro)tin(IV) complex of 3, after evaporation.

18: $^1$H NMR (CD$_3$OD): δ=10.04 (s, 1H), 9.04 (d, $^3$J(H, H)=4.8 Hz, 1H), 8.96 (s, 1H), 8.94 (d, $^3$J(H,H)=5.2 Hz, 1H), 8.84 (d, $^3$J(H,H)=4.3 Hz, 2H); $^{19}$F NMR (CD$_3$OD): δ=−135.1 (m, 2F), −136.8 (m, 4F), −151.8 (t, $^3$J(F,F)=20.2

Hz, 1F), −152.4 (t, $^3$J(F,F)=20.0 Hz, 1F), −154.7 (t, $^3$J(F,F)=20.0 Hz, 1F), −161.2 (m, 4F), −164.3 (m, 2F); UV/Vis (MeOH): $\lambda_{max}$ ($\epsilon$) 424 nm (140000), 582 (16000), 602 (18000); MS (FAB$^-$): m/z: 1107.38 [M$^-$].

5.5 Insertion of Chromium(III): One portion of CrCl$_2$ (40 mg, 0.33 mmol) was added at once to a 10 mL pyridine solution of 3 (14 mg, 15 μmol) and the mixture was heated immediately to reflux for 30 min. The solvent was evaporated and inorganic salts were removed via column chromatography on silica (eluent: MeOH:pyridine=20:1). Dissolving the dried product in CH$_2$Cl$_2$, filtration and solvent evaporation, afforded 16 mg (14 μmol, 93% yield) of compound 19, the (bis-pyridine)chromium(III) complex of 3.

19: UV/Vis (MeOH/pyridine 5%): $\lambda_{max}$ ($\epsilon$) 320 nm (11000), 420 (19000), 434 (22000), 476 (6300), 542 (3700), 586 (5100), 614 (6300), 648 (7300).

5.6 Insertion of Iron(III): One portion of FeCl$_2$ (100 mg, 0.79 mmol) was added at once to a 10 mL pyridine solution of compound 3 (30 mg, 31 μmol) and the mixture was heated immediately to reflux for 15 min under argon, followed by evaporation of the solvent. The inorganic salts were separated by column chromatography on silica (eluent: EtOH), affording 33 mg (28 μmol, 90% yield) of compound 20, the iron(III) bis-pyridine complex of 3.

20: UV/Vis (buffer phosphate solution, pH=7.00) $\lambda_{max}$ ($\epsilon$(M$^{-1}$ cm$^{-1}$))=404 (34000), 552 (12000), 738 (2300).

$^{19}$F NMR (CD$_3$OD): δ=−101.8 (brs, ortho-F), −105.3 (brs, ortho-F), −115.1 (brs, ortho-F), −149.0 (s, para-F), 149.8 (s, para-F), −154.3 (s, para-F), −155.5 (s, meta-F), −156.6 (s, meta-F), −159.8 (s, meta-F).

Example 6

Nitration of Metal Complexes of Compound 1

Compounds 6–8 were prepared by nitration of 5, the gallium complex of compound 1, as described in Examples 6a–6c, and compound 32 was prepared by nitration of the tin complex of compound 1, as described in Example 6d:

6a. Conditions for mono-nitration: Compound 5 (40 mg, 0.04 mmol), sodium nitrite (290 mg, 4 mmol), and dry acetonitrile (5 mL) were placed in a two necked flask and the suspension was stirred for 10 min under Ar. Tris(4-bromophenyl)aminium hexachloroantimonate (24 mg, 0.03 mmol, 75 mol %) was added and stirring was continued for 1 h at room temperature, after which the solvent was evaporated to dryness. The crude material was separated and purified on a silica gel column eluted with 20% ethylacetate in hexane, as to provide two fractions (R$_f$=0.43 (major) and R$_f$=0.26 (minor) on silica with hexane:ethylacetate/3:2). Recrystallization from dichloromethane/hexane of the two fractions afforded 38 mg (84% yield) of compound 6, 3-nitro-5,10,15-tris(pentafluorophenyl)corrolato gallium (III)(bis-pyridine) and 4 mg (8.9% yield) of compound 7, 3,17-dinitro-5,10,15-tris(pentafluorophenyl)corrolato gallium(III)(bis-pyridine).

6: $^1$H NMR (CDCl$_3$): δ=9.69 (s, 1H), 8.71 (d, $^3$J(H,H)=4.1 Hz, 1H), 8.61 (t, $^3$J(H,H)=5.1 Hz, 2H), 8.45 (d, $^3$J(H,H)=4.1 Hz, 1H), 8.32 (d, $^3$J(H,H)=4.6 Hz, 2H), 6.01 (t, $^3$J(H,H)=7.7 Hz, 2H), 5.89 (m, 4H), 5.55 (t, $^3$J(H,H)=6.2 Hz, 4H); $^{19}$F NMR (CDCl$_3$): δ=−139.07 (t, $^3$J(F,F)=12.6 Hz, 4F), −140.38 (dd, $^3$J(F,F)=24.6 Hz, $^4$J(F,F)=6.7 Hz, 2F), −152.15 (td, $^3$J(F,F)=21.9 Hz, $^4$J(F,F)=5.2 Hz, 2F), −153.59 (t, $^3$J(F,F)=21.4 Hz, 1F), −161.95 (m, 4F), −163.5 (td, $^3$J(F,F)=23.1 Hz, $^4$J(F,F)=6.9 Hz, 2F); UV/Vis (EtOAc): $\lambda_{max}$ ($\epsilon$ 101000), 612 (30000); MS (DCI$^-$): m/z: 906.9 [M−2 pyridine]$^-$.

7: $^1$H NMR (CDCl$_3$): δ=9.54 (s, 2H); 8.61 (d, $^3$J(H,H)=4.57 Hz, 2H), 8.35 (d, $^3$J(H,H)=4.6 Hz, 2H), 7.35 (t, $^3$J(H,H)=7.62 Hz, 2H), 6.60 (t, $^3$J(H,H)=6.06 Hz, 4H), 6.3 (br s, 4H); $^{19}$F NMR (CDCl$_3$): δ=−139.04 (dd, $^3$J(F,F)=19.9 Hz, $^4$J(F,F)=6.7 Hz, 2F), −140.53 (dd, $^3$J(F,F)=18.0 Hz, $^4$J(F,F)=6.7 Hz, 4F), −150.86 (t, $^3$J(F,F)=21.4 Hz, 1F), −152.06 (t, $^3$J(F,F)=21.2 Hz, 2F), −161.37 (td, $^3$J(F,F)=22.1 Hz, $^4$J(F,F)=6.2 Hz, 2F), −162.58 (td, $^3$J(F,F)=22.1 Hz, $^4$J(F,F)=6.5 Hz, 4F); UV/Vis (EtOAc): $\lambda_{max}$ 324 nm ($\epsilon$ 26500), 380 (17000), 460 (46200), 644 (31000); MS (DCI$^-$): m/z: 951 [M−bis-Py]$^-$.

6b. Conditions for bis-nitration: The same reaction conditions as above were utilized, but with more tris(4-bromophenyl)aminium hexachloroantimonate (68.8 mg, 0.08 mmol, 200 mol %). The crude material was separated and purified on a silica gel column eluted with 20% ethylacetate in hexane, as to provide three fractions: 6 (2%), 7 (94%), and traces of compound 8, 3,17,18-trinitro-5,10,15-tris (pentafluorophenyl)corrolato gallium(III)(bis-pyridine) (R$_f$=0.12 on silica with hexane:ethylacetate/3:2).

6c. Conditions for tris-nitration: Using identical reaction conditions as above, but with 300 mol % tris(4-bromophenyl)aminium hexachloroantimonate (0.103 mg, 0.12 mmol), the crude material was separated and purified on a silica gel column eluted with 20% ethylacetate in hexane, as to provide three fractions: 6—traces, 7 (58.4%) and 8 (26.6%).

8: $^1$H NMR (CDCl$_3$): δ=9.84 (s, 1H), 8.44 & 8.39 (overlapping doublets, 2H), 8.18 & 8.14 (overlapping doublets, 2H), 7.36 (t, $^3$J(H,H)=7.6 Hz, 2H), 6.81 (br s, 4H), 6.08 (br s, 4); $^{19}$F NMR (CDCl$_3$): δ=−138.23 (m, 4F), −139.95 (d, $^3$J(F,F)=16.1 Hz, 2F), −149.24 (t, $^3$J(F,F)=20.4 Hz, 1F), −150.93 (t, $^3$J(F,F)=20.8 Hz, 1F), −152.04 (t, $^3$J(F,F)=20.7 Hz, 1F), −160.65 (t, $^3$J(F,F)=20.4 Hz, 4F), −161.98 (t, $^3$J(F,F)=20.6 Hz, 2F); UV/Vis (EtOAc): $\lambda_{max}$ 326 nm ($\epsilon$ 25000), 416 (42000), 456 (31000), 616 (29000),668 (28000); MS (DCI$^-$): m/z: 997 M−bis-Py]$^-$.

6d Preparation of compound 32: When the reaction was performed on the (chloro)tin(IV) complex of corrole 1 with 75 mol % of oxidant, the mono-nitrated product 32 was obtained in 63% yield.

32: $^1$H NMR (CDCl$_3$): δ=9.81 (s, 1H), 9.16 (d, $^3$J(H,H)=4.2 Hz, 1H), 8.76 (m, 3H), 8.54 (m, 2H); $^{19}$F NMR (CDCl$_3$): δ=−136.85 (d, $^3$J(F,F)=23.5 Hz, 2F), −137.82 (d, $^3$J(F,F)=23.8 Hz, 1F), −137.92 (d, $^3$J(F,F)=22.9 Hz, 1F), −139.13 (d, $^3$J(F,F)=19 Hz, 2F), −151.10 (t, $^3$J(F,F)=20.7 Hz, 1F), −151.45 (t, $^3$J(F,F)=20.9 Hz, 1F), −152.78 (t, $^3$J(F,F)=20.9 Hz, 1F), −161.18 (m, 4F), −162.54 (td, $^3$j(F,F)=23.5 Hz, $^4$J(F,F)=7.5 Hz, 2F); MS (DCI$^-$): m/z: 992 [M+Cl]$^-$.

Example 7

Preparation of Compounds 9–10 by Formylation of 5

7a. Conditions for mono-substitution: DMF (0.16 mL) was cooled to 5–10° C., POCl$_3$ (0.12 mL, 1.16 mmol) was added under N$_2$ and the mixture was stirred for 15 minutes. The ice bath was removed and the solution was stirred for another 15 minutes. Dry dichloromethane (4 mL) was then added and the reagent was cooled to 0–5° C. A limited amount of the reagent (0.428 mL) was added dropwise to a solution of 5 (100 mg, 0.106 mmol) in 8 mL of CH$_2$Cl$_2$. During addition, the solution turned from red to deep green, and after 3–5 min TLC (silica, CH$_2$Cl$_2$:hexane, 2:1, and some drops of pyridine) showed no starting material. A saturated solution of Na$_2$CO$_3$ (50 mL) was added and the mixture was stirred overnight, after which the organic phase was separated. The water phase was extracted by $CH_2Cl_2$ three times, the organic phases were combined, washed by brine, dried by $Na_2SO_4$ and the solvents were evaporated. Column chromatography on silica (eluent: $CH_2Cl_2$:hexane:pyridine, which was gradually changed from 100:20:0.2 to 60:100:0.4) afforded compound 9, 3-formyl-5,10,15-tris(pentafluorophenyl)corrolato gallium (III)(pyridine) as green-blue crystals (yield 0.091 g, 87% after recrystallization from $CH_2Cl_2$, hexane and some drops of pyridine).

9: $^1$H NMR (CDCl$_3$): δ 10.52 (s, 1H, CHO); 9.65 (s, 1H, α-CHO); 9.11 (d, $^3$J(H,H)=4.1 Hz, 1H); 8.76 (d, $^3$J(H,H)=4.7 Hz, 1H); 8.73 (d, $^3$J(H,H)=4.1 Hz, 1H); 8.67 (d, $^3$J(H,H)=4.8 Hz, 1H); 8.52 (d, $^3$J(H,H)=4.8 Hz, 1H); 8.48 (d, $^3$J(H,H)=4.7 Hz, 1H); 6.77 (tt, $^3$J(H,H)=7.7 Hz, $^4$J(H,H)=1.5 Hz, 1H); 6.00 (td, $^3$J(H,H)=6.6 Hz, $^4$J(H,H)=1.24 Hz, 2H); 3.29 (d, $^3$J(H,H)=5.0 Hz, 2H). $^{19}$F NMR (CDCl$_3$): δδ−138.1 (m (overlapping doublet), 4F); −138.96 (dd, $^3$J(F,F)=24.16 Hz, $^4$J(F,F)=8.27 Hz, 2F); −153.02 (t, $^3$J(F,F)=20.34 Hz, 1F); −153.05 (t, $^3$J(F,F)=20.68 Hz, 1F); −153.38 (t, $^3$J(F,F)=21.24 Hz, 1F); −162.4 (m, 6F). UV/Vis (CH$_2$Cl$_2$): λ$_{max}$ (ϵ(M$^{-1}$ cm$^{-1}$))=410 nm (41277), 432 (171481), 602 (24630), 620 (28591). IR (CHCl$_3$, cm$^{-1}$): 1653 (CO). MS (DCI$^+$): m/z (%): 891 ([M$^+$], 100). MS (DCI$^-$): m/z (%): 890 ([M], 100), 862 ([M−CO], 20). R$_f$=0.18 (CH$_2$Cl$_2$:hexane, 2:1, and some drops of pyridine).

Further elution by CH$_2$Cl$_2$:pyridine (100:0.5) gives compound 10, 2,17-bisformyl-5,10,15-tris(pentafluorophenyl) corrolato gallium(III)(bis-pyridine) (yield 0.004 g, 3.5% after recrystallization from CH$_2$Cl$_2$, hexane and some drops of pyridine).

10: $^1$H NMR (CDCl$_3$): δ 11.13 (s, 1H, CHO); 10.57 (s, 1H, CHO); 10.03 (s, 1H, α-CHO); 9.01 (s, 1H, α-CHO); 8.67 (d, $^3$J(H,H)=4.76 Hz, 1H); 8.60 (d, $^3$J(H,H)=4.78 Hz, 1H); 8.38 & 8.37 (overlapping doublets, 2H); 7.04 (td, $^3$J(H,H)=7.68, $^4$J(H,H)=1.6 Hz, 2H); 6.33 (t, $^3$J(H,H)=7.06, 4H); 4.33 (br s, 4H). $^{19}$F N (CDCl$_3$): δ−138.08 (m, 4F); −139.57 (dd, $^3$J(F,F)=23.97, $^4$J(F,F)=8.08 Hz, 2F); −152.15 (t, $^3$J(F,F)=42.49 Hz, 1F); −152.74 (t, $^3$J(F,F)=42.11 Hz); −153.05 (t, $^3$J(F,F)=42.11 Hz, 1F); −161.48 (dt, $^3$J(F,F)=43.43 Hz, $^4$J(F,F)=7.33 Hz, 2F); −161.87 (dt, $^3$J(F,F)=44.46 Hz, $^4$J(F,F)=7.52 Hz, 2F); −162.71 (dt, $^3$J(F,F)=44.84 Hz, $^4$J(F,F)=7.33 Hz, 2F). UV/Vis (CH$_2$Cl$_2$): λ$_{max}$ (ϵ(M$^{-1}$ cm$^{-1}$))=416 nm (20741), 436 (57064), 612 (16364), 636 (16170). IR (CHCl$_3$, cm$^{-1}$): 1674 (CO). MS (DCI$^+$): m/z (%): 919 ([M$^+$], 100). MS (DCI$^-$): m/z (%): 918 ([M$^-$], 100), 890 ([M$^-$−CO], 40). R$_f$=0.11 (CH$_2$Cl$_2$:Hexane, 2:1, and some drops of pyridine).

7b. Conditions for bis-substitution: DMF (1.6 mL) was cooled to 5–10° C., POCl$_3$ (1.22 mL, 11.6 mmol) was added under N$_2$ and the mixture was stirred for 15 minutes. The ice bath was removed and the solution was stirred for another 15 minutes. Dry dichloromethane (2 mL) was then added and the reagent was cooled to 0–5° C. This solution was added dropwise to a solution of 5 (100 mg, 0.106 mmol) in 2 mL of CH$_2$Cl$_2$. During addition, the solution turned from red to deep green, and after 3–5 min TLC (silica, CH$_2$Cl$_2$:Hexane, 2:1, and some drops of pyridine) showed no starting material. A saturated solution of Na$_2$CO$_3$ was added and the mixture was stirred overnight, after which the organic phase was separated. The aqueous phase was extracted by CH$_2$Cl$_2$, the organic phases were collected and washed by brine, dried by Na$_2$SO$_4$ and solvents were evaporated. Column chromatography on silica (eluent:CH$_2$Cl$_2$:hexane:pyridine, which was gradually changed from 100:20:0.2 to 0:100:0.4) afforded 9 as green-blue crystals (yield 0.015 g, 15% after recrystallization from CH$_2$Cl$_2$, hexane and some drops of pyridine). Further elution by CH$_2$Cl$_2$:pyridine (100:0.5) provides 10 (yield 0.075 g, 64% after recrystallization from CH$_2$Cl$_2$, hexane and some drops of pyridine).

Example 8

Formylation of Metal Complexes of Compound 1

The Al(III),[8b] Co (III),[16b] and Mn(III) complexes of compound 1,[6b,d] were reacted with the Vilsmeier reagent and compounds 24–28 were obtained as presented in Table 1 (preliminary results). All reactions were performed with 100 equivalents of reagent. In the Table: tpfc=compound 1.

TABLE 1

Formylation of metal complexes of 1 (preliminary results).

| Substrate | Major product, isolated yield (%). | Minor product, isolated yield (%). |
|---|---|---|
| (Py)Al(tpfc) | 24: Bis-substituted, 91% | — |
| (Py)$_2$Co(tpfc) | 26: Tris-substituted, 55% | 25: Bis-substituted (?), 25% |
| Mn(tpfc) | 28: Bis-substituted, 75% | 27: Mono-substituted, 16% |

24 (Py)$_2$Al(tpfc-(CHO)$_2$):

Ms (DCI$^-$): m/z (%): 876 ([M], 100), 848 ([M−CO], 40). UV/vis (CH$_2$Cl$_2$): λ$_{max}$ 415 nm, 435, 616, 630. $^1$H NMR (CDCl$_3$): δ 10.83 (s, 1H, CHO); 10.39 (s, 1H, CHO); 9.63 (s, 1H, α-CHO); 8.82 (s, 1H, α-CHO); 8.53 (d, $^3$J(H,H)=4.3 Hz?, 1H); 8.43 (d, $^3$J(H,H)=4.3 Hz?, 1H); 8.21 (br s, 2H), 7.09 (t, $^3$J(H,H)=7.3 Hz, 2H); 6.45 (t, $^3$J(H,H)=5.7 Hz, 4H); 5.38 (br s, 4H). $^{19}$F NMR (CDCl$_3$): δ −138.22 (d, $^3$J(F,F)=17 Hz, 4F); −139.58 (d, $^3$J(F,F)=20.8 Hz, 2F); −152.72 (t, $^3$J(F,F)=22.4 Hz, 1F); −153.42 (m, 2F); −161.78 (td, $^3$J(F,F)=?, $^4$J(F,F)=?, 2F); −162.3 (td, $^3$J(F,F)=?, $^4$J(F,F)=?, 2F); −162.786 (td,$^3$J(F,F)=?, $^4$J(F,F)=?, 2F).

26 (Py)$_2$Co(tpfc-(CHO)$_3$):

Ms (DCI$^-$): m/z (%): 936.6 ([M], 100), 880.9 ([M−2CO], 40). UV/vis (CH$_2$Cl$_2$): λmax 443 nm, 629, 704. $^1$H NMR (CDCl$_3$): δ 11.45 (s, 1H, CHO); 10.46 (s, 1H, CHO); 10.33 (s, 1H, α-CHO); 9.95 (s, 1H, α-CHO); 8.43 (d, $^3$J(H,H)=4.8 Hz, 1H); 8.37 (d, $^3$J(H,H)=5 Hz, 1H); 8.22 (d, $^3$J(H,H)=4.8 Hz, 1H); 8.17 (d, $^3$J(H,H)=4.8 Hz, 1H); 6.38 (t, $^3$J(H,H)=?, 2H); 5.5 (br s, 4H); 2.55 (d, $^3$J(H,H)=4.9 Hz, 4H). $^{19}$F NMR (CDCl$_3$): δ −138.46 (d, $^3$J(F,F)=8.6 Hz, 1F); −138.61 (d, $^3$J(F,F)=8.6 Hz, 1F); −138.81 (d, $^3$J(F,F)=8 Hz, 1F); −138.93 (d, $^3$J(F,F)=8.4 Hz, 1F); −140.38 (d, $^3$J(F,F)=7.6 Hz, 1F); −140.51 (d, $^3$J(F,F)=7.6 Hz, 1F); −151.05 (t, $^3$J(F,F)=22.4 Hz, 1F); −152.735 (t, $^3$J(F,F)=22 Hz, 1F); −153.07 (t, $^3$J(F,F)=22.2 Hz, 1F); −161.04 (td, $^3$J(F,F)=23.6 Hz, $^4$J(F,F)=8 Hz, 2F); −161.84 (td, $^3$J(F,F)=22.7 Hz, $^4$J(F,F)=9 Hz, 2F); −162.71 (td, $^3$J(F,F)=24 Hz, $^4$J(F,F)=6 Hz, 2F).

27: Mn(tpfc-CHO):

Ms (DCI$^-$): m/z (%): 875.9 ([M], 100). UV/vis (CH$_2$Cl$_2$): λ$_{max}$ 421 nm, 480, 614, 659. $^{19}$F NMR (CDCl$_3$): δ −120.21 (br s, 4H); −128.267 (br s, 2H); −150.92 (s, 1H), −152.137 (s, 1H); −153.24 (s, 1H); −156.74 (s, 2H); −157.54 (s, 2H); −158.32 (s, 2H).

28: Mn(tpfc-(CHO)$_2$):

Ms (DCI$^-$): m/z (%): 903.8 ([M], 100). UV/vis (CH$_2$Cl$_2$): λ$_{max}$ 421 nm, 488, 655, 678.

Example 9

Crystallography

The crystalline samples of 6 and 8 were covered with a thin layer of light oil and cooled between −163° C. to −158° C., in order to minimize the escape of volatile crystallization solvents and minimize thermal motion/structural disorder effects. Crystal structures of 7 and 14 were analysed at room temperature. The intensity data were corrected for absorption. The structures were solved by direct methods (SHELXS-86 and SIR-92),[17] and refined by full-matrix least-squares on $F^2$ (SHELXL-97).[18] All non-hydrogen atoms of the corroles were refined anisotropically. The hydrogens were located in idealized positions, and were refined using a riding model with fixed thermal parameters [$U_{ij}$=1.2 $U_{ij}$ (eq.) for the atom to which they are bonded]. The four corrole compounds 6, 7, 8 and 14, co-crystallized with additional guest/solvent components trapped, and severely disordered, in the lattice. In addition, partial rotational disorder characterizes some of the pentafluorophenyl rings of the corroles (as it is demonstrated in particular by excessively large thermal displacement parameters of the corresponding atoms), affecting to some extent (particularly in 7 and 8) the precision of the crystallographic determination. Yet, in all cases the crystallographic analysis provided an unequivocal description of the respective molecular structures, adding confidence to the conclusions based on the spectroscopic analyses.

Crystal Data:

6: $C_{42}H_{12}F_{15}GaN_6O_2.(C_6H_6)$, M=1065.4, orthorhombic, space group $P2_12_12_1$, a=12.0410(2), b=18.2040(3), c=18.5900(3) Å, V=4074.8(1) Å$^3$, Z=4, T=110(2) K, $D_c$=1.737 g·cm$^{-3}$, $\mu$(MoKα)=0.80 mm$^{-1}$, 5283 unique reflections to $2\theta_{max}$=55.7°, 662 refined parameters, $R_1$=0.046 for 4374 observations with I>2σ(I), $R_1$=0.064 (w$R_2$=0.113) for all unique data. Molecules of the benzene solvent exhibit an in-plane rotational disorder, with was modeled by two possible orientations with occupancy factors of 0.71(3) for the major site and and 0.29 for the minor one. This compound crystallized as a racemic twin.

7: $C_{47}H_{12}F_{15}GaN_8O_4.NaNO_3$, M=1196.4, monoclinic, space group $P2_1/c$, a=17.9080(4), b=12.5160(2), c=25.1330 (5) Å, β=122.650(2)°, V=4743.1(2) Å$^3$, Z=4, T=293(2) K, $D_c$=1.675 g·cm$^3$, $\mu$(MoKα)=0.71 mm$^{-1}$, 8117 unique reflections to $2\theta_{max}$=50.0°, 738 refined parameters, $R_1$=0.069 for 2987 observations with I>2σ(I), $R_1$=0.158 (w$R_2$=0.181) for all unique data. The experimental measurements were carried out in this case at room temperature, at which the analyzed crystal exhibited somewhat poor diffraction due to a considerable disordered guest species.

8: $C_{42}H_{10}F_{15}GaN_8O_6.CH_2Cl_2.C_6H_{12}$, M=1246.4, monoclinic, space group $P2_1/c$, a=11.3990(3), b=19.0230 (4), c=22.7610(6) Å, β=104.564(1)°, V=4777.0(2) Å$^3$, Z=4, T=110(2) K, $D_c$=1.733 g·cm$^{-3}$, $\mu$(MoKα)=0.81 mm$^{-1}$, 10262 unique reflections to $2\theta_{max}$=55.7°, 799 refined parameters, $R_1$=0.101 for 6276 observations with I>2σ(I), $R_1$=0.160 (w$R_2$=0.312) for all unique data. The crystals turned out to be partly twinned. Moreover, the dichloromethane and hexane solvent species are severely disordered in the crystal lattice even at the low temperature and could not be reliably modeled and refined. The pentafluorophenyl rings also exhibit large-amplitude thermal motion about axes connecting them to the main corrole ring. Hence the relatively high R factors.

14: $C_{65}H_{41}CoF_{15}N_6O_4PS_2.C_6H_6$, M=1487.2, triclinic, space group P-1, a=13.827(3), b=13.815(3), c=18.209(4) Å, α=76.76(2), β=79.18, γ=70.13(2)°, V=3161.2(12) Å$^3$, Z=2, T=293(2) K, $D_c$=1.562 g·cm$^{-3}$, $\mu$(MoKα)=0.46 mm$^{-1}$, 8592 unique reflections to $2\theta_{max}$=46.0°, 799 refined parameters, $R_1$=0.105 for 5128 observations with I>2σ(I), $R_1$=0.167 (w$R_2$=0.270) for all unique data. The crystal of this compound were diffracting poorly due to wide-amplitude thermal motion of the included solvent and the various substituents on the corrole ring.

Example 9

Preparation of Compounds 21, 22 and 31

Compounds 21 and 22 we prepared by reaction of compound 5 with phosgene. A solution of phosgene (0.12 mL, 1.2 mmol) in toluene (0.6 mL) was added to a stirred solution of 5 (0.115 g, 0.12 mmol) and pyridine (0.02 g, 0.24 mmol) in toluene (7 mL) over 10 minutes at 0° C. The solution was stirred at 0–5° C. for 30 min, after which it was quenched with ice and water and extracted with dichloromethane. The organic layer was washed with water three times, dried over anhydrous sodium sulfate, filtered and evaporated. The crude material (the —COCl adduct of the corrole, compound 21) was separated and purified via elution with 30% ethyl acetate in hexane on a short silica gel column, as to provide compound 22, the 5,10,15-tris (pentafluorophenyl)corrolato gallium(III)(pyridine) 3-carboxylic acid, as blue-red crystals (yield: 0.052 g, 42%), $R_f$=0.53 on silica with hexane:ethylacetate/3:2).

22: $^1$H NMR ($C_6D_6$): δ=10.09 (s, 1H), 8.91 (d, 3J(H,H)= 3.8 Hz, 1H), 8.83 (d, $^3$J(H,H)=4.4 Hz, 1H), 8.75 (d, $^3$J(H, H)=4.1 Hz, 1H), 8.57 (d, 3J(H,H)=3.5 Hz, 1H),8.52 (t, $^3$J(H,H)=4.0 Hz, 2H), 5.31 (t, $^3$J(H,H)=6.9 Hz, 1H), 4.77 (m, 2H), 3.9 (m, 2H); $^{19}$F NMR ($C_6D_6$): δ=−138.82 (d, $^3$J(F,F)= 24.1 Hz, 4F), −139.96 (dd, $^3$J(F,F)=24.1 Hz, $^4$J(F,F)=5.6 Hz, 2F), −152.94 (td, $^3$J(F,F)=20.5 Hz, $^4$J(F,F)=6.7 Hz, 2F), −155.6 (t,$^3$J(F,F)=21 Hz, 1F), −162.2 (m, 4F), −164.8 (t,$^3$J (F,F)=20.5 Hz, 2F).

Compound 31, the methyl ester of compound 22, was prepared in quantitative yield by reaction of compound 22 with methanol in the presence of 1-[3-(dimethylamino) propyl]-3-ethylcarbodiimide hydrochloride [CAS # 25952-53-8].

31: $^1$H NMR ($C_6D_6$): δ=9.79 (s, 1H), 9.04 (d, $^3$J(H,H)=4.1 Hz, 1H), 8.87 (t, $^3$J(H,H)=5.3 Hz, 2H), 8.67 (d, $^3$J(H,H)=4.0 Hz, 1H), 8.58 (d, $^3$J(H,H)=4.5 Hz, 2H), 4.98 (t, $^3$J(H,H)=6.9 Hz, 1H), 4.40 (m, 2H), 2.9 (m, 2H); MS (DCI$^{-1}$): m/z: 920 [M−pyridine]$^-$.

Scheme 1
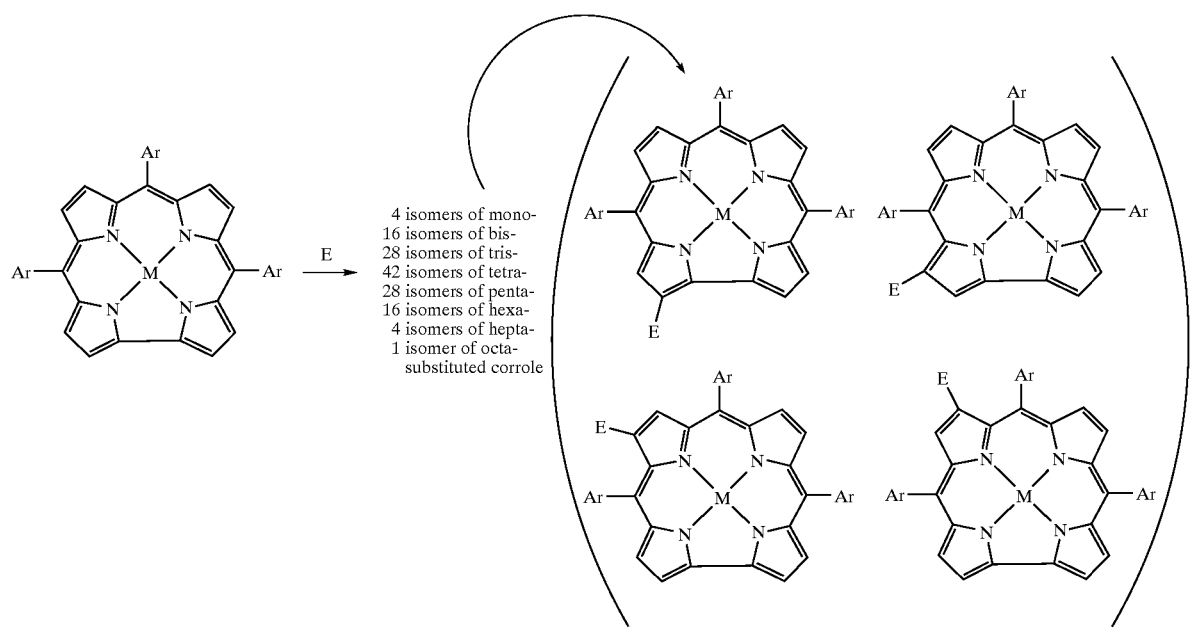
1: Ar = C$_6$F$_5$, M = 3H
4: Ar = C$_6$F$_5$, M = Ga
E: electrophile
Scheme 2
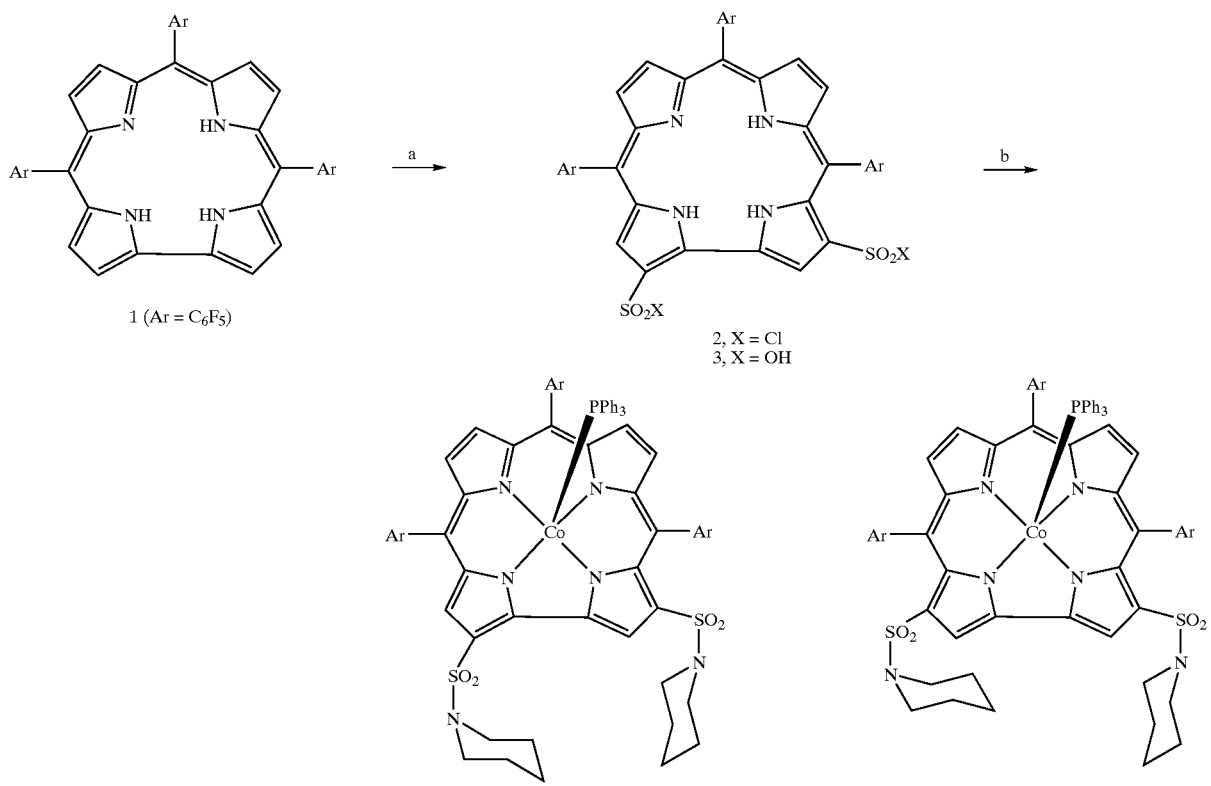
1 (Ar = C$_6$F$_5$)
2, X = Cl
3, X = OH
13 (72% yield from 1)      14 (3% yield from 1)
a. 1 -> 2: ClSO$_3$H, 5 min, 2 -> 3: H$_2$O, reflux/12 h,
b. 1) piperidine/RT  2) Co(OAc)$_2$·4H$_2$O, pyridine/reflux, PPh$_3$ Scheme 3

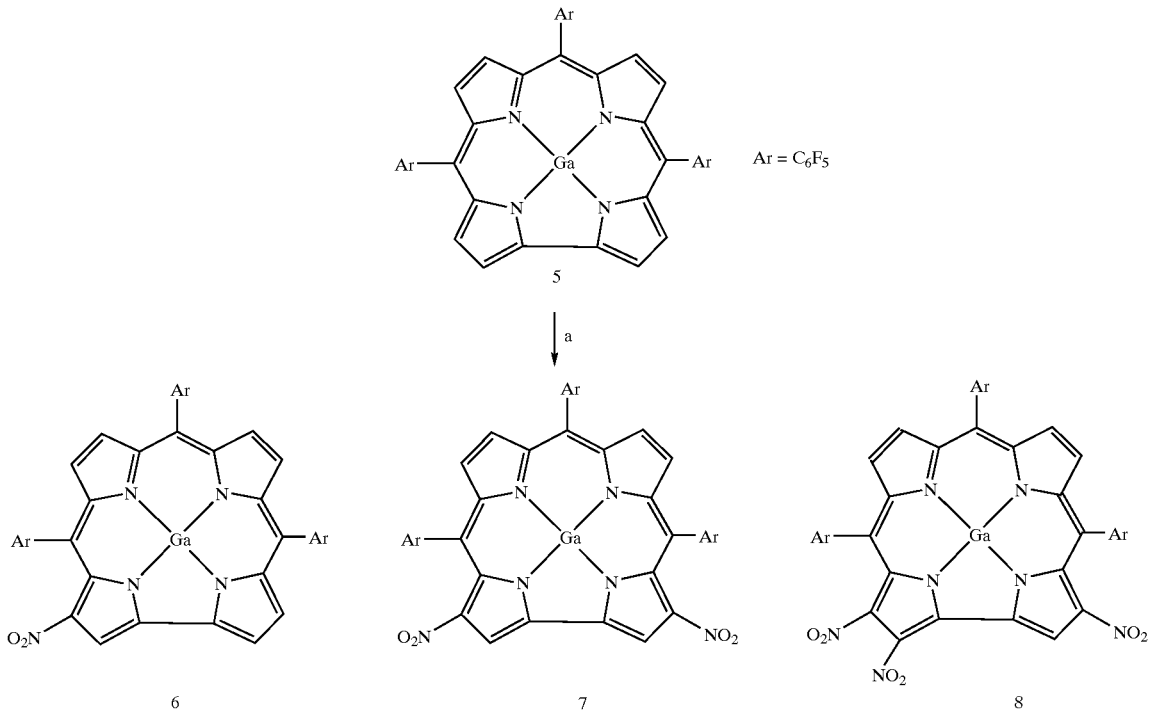

a. 40 mmol 4, 4 µmol NaNO$_2$, 5 mL•CH$_3$CN, Ar, + (Ar$_3$N$^+$)(SbCl$_6^-$) (5, Ar = 4-bromopher
 30 µmol 5: 84% 6, 9% 7
 80 µmol 5: 2% 6, 94% 7, <1% 8
 120 µmol 5: <1% 6, 58% 7, 27% 8

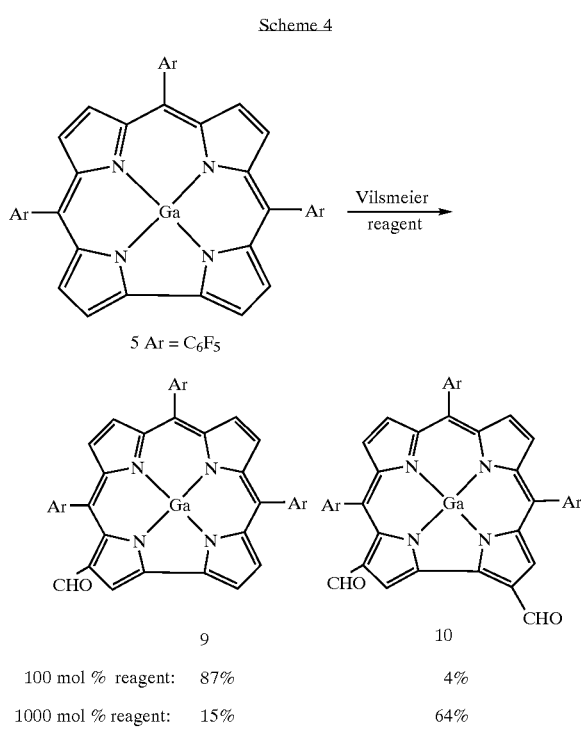

Scheme 4

| | 9 | 10 |
|---|---|---|
| 100 mol % reagent: | 87% | 4% |
| 1000 mol % reagent: | 15% | 64% |

References 1. (a) *Expanded, Contracted, & Isomeric Porphyrins*; Sessler, J. L.; Weghorn, S. J., Eds.; Pergamon: Oxford, 1997, chapter 1. (b) Paolesse, R. In *The Porphyrin Handbook*, Vol. II.; Kadish, K. M., Smith, K. M., Guilard, R. Eds.; Academic Press: New York, 2000, chap. 11; pp. 201–232.
2. (a) Loim, N. M.; Grishko, E. V.; Pyshnograeva, N. I.; Vorontsov, E. V.; Sokolov, V. I. *Izv. Akad Nauk. Ser. Khim.* 1994, 5, 925. (b) Rose, E.; Kossanyi, A.; Quelquejeu, M.; Soleihavoup, M.; Duwavran, F.; Bernard, N.; Lecas, A. *J. Am. Chem. Soc.* 1996 118, 1567. (c) Tse, M. K.; Zhang, Z.; Mak, T. C. W.; Chan, K. S. *Chem. Commun.* 1998, 1199.
3. (a) Gross, Z.; Galili, N.; Saltsman, I. *Angew. Chem. Int. Ed. Engl.* 1999, 38, 1427. (b) Gross, Z.; Galili, N.; Simkhovich, L.; Saltsman, I.; Botoshansky, M.; Blaser, D.; Boese, R.; Goldberg, I. *Org Lett.* 1999, 1, 599.
4. (a) Paolesse, R.; Jaquinod, L.; Nurco, D. J.; Mini, S.; Sagone, F.; Boschi, T.; Smith, K. M. *Chem. Commun.* 1999, 1307. (b) Simkhovich, L.; Goldberg, I.; Gross, Z. *J. Inorg. Biochem.* 2000, 80, 235. (c) Cho, W.-S.; Lee, C.-H. *Tetrahedron Lett.* 2000, 41, 697. (d) Gryko, D. T. *Chem. Commun.* 2000, 2243. (e) Briñas, R P.; Brückner, C. *Synlett.* 2001, 442. (f) Gryko, D. T.; Jadach, K. *J. Org. Chem.* 2001, 66, 4267. (g) Ka, J.-W.; Cho, W.-S.; Lee, C.-H. *Tetrahedron Lett.* 2000, 41, 8121. (h) Paolesse, R.; Nardis, S.; Sagone, F.; Khoury, R. G. *J. Org. Chem.* 2001, 66, 550. (i) Asokan, C. V.; Smeets, S.; Dehaen, W. *Tetrahedron Lett.* 2001, 42, 4483.
5. *Expanded, Contracted, & Isomeric Porphyrins*; Sessler, J. L.; Weghorn, S. J., Eds.; Pergamon: Oxford, 1997, chapter 10. (b) *Metalloporphyrins Catalyzed Oxidations*; Montanari, F.; Casella, L., Eds.; Kluwer Academic Publishers: Dordrecht, 1994. (c) Sternberg, E. D.; Dolphin, D.; Bruckner, C. *Tetrahedron* 1998, 54, 4151.
6. (a) Gross, Z.; Simkhovich, L.; Galili, N. *Chem. Commun.* 1999, 599. (b) Gross, Z.; Golubkov, G.; Similkovich, L. *Angew. Chem. Int. Ed. Eng.* 2000, 39, 4045. (c) Simihovich, L.; Mahammed, A.; Goldberg, I.; Gross, Z. *Chem. Eur. J.* 2001, 7, 1041. (d) Golubkov, G.; Bendix, J.; Gray, H. B.; Mahammed, A.; Goldberg, I.; DiBilio, A. J.; Gross, Z. *Angew. Chem. Int. Ed. Eng.* 2001, 40, 2132. (e) Simkhovich, L; Gross, Z. *Tetrahedron Lett.* 2001, 42, 8089. (f) J. Grodkowski, P. Neta, E. Fujita, A. Mahammed, L. Simkhovich, and Z. Gross, *J. Phys. Chem. A* 2002, 106, 4772–4778.
7. Aviezer, D.; Cotton, S.; David, M.; Segev, A.; Khaselev, N.; Galili, N.; Gross, Z.; Yayon, A. *Cancer Research*, 2000, 60, 2973.
8. (a) Bendix, J.; Dmochowski, I. J.; Gray, H. B.; Mahammed, A.; Simkhovich, L.; Gross, Z. *Angew. Chem. Int. Ed. Eng.* 2000, 39, 4048. (b) Mahammed, A., Gross, Z. *J. Inorg. Biochem.* 2002, 88, 305–309. (c) D. Aviezer, A. Yayon, Z. Gross (Yeda Res & Dev and Technion Res & Dev Foundation); "Pharmaceutical Compositions Comprising Porphyrins and some Novel Porphyrin Derivatives", International Publication Date: 18.5.00 (WO 00/27379).
9. (a) Gross, Z., *J. Biol. Inorg. Chem.* 2001, 6, 733. (b) Erben, C.; Will, S.; Kadish, K. M. In *The Porphyrin Handbook*, Vol. II.; Kadish, K. M., Smith, K. M., Guilard, R. Eds.; Academic Press: New York, 2000, chap. 12; pp. 233–300.
10. Johnson, A. W.; Kay, I. T. *J. Chem. Soc.* 1965, 1620.
11. Gross, Z.; Galili, N. *Angew. Chem. Int. Ed. Eng.* 1999, 38, 2366. (b) Simkhovich, L.; Goldberg, I.; Iyer, P.; Gross, Z. *Chem. Eur. J.* 2002, 8, 2595–2601.
12. For formylation of the meso-positions of corroles, see: Paolesse, R.; Jaquinod, L.; Senge, M. O.; Smith, K. M. *J. Org. Chem.* 1997, 62, 6193.
13. Bartoli, J. F.; Battioni, P.; De Foor, W. R.; Mansuy, D. *J. Chem. Soc., Chem. Commun.* 1994, 23. Ozette, K.; Leduc, P.; Palacio, M.; Bartoli, J.-F.; Barkigia, K. M.; Fajer, J.; Battioni, P.; Mansuy, D. *J. Chem. Soc.* 1997, 119, 6442. Garcia-Ortega, H.; Ribo, J. M. *J. Porphyrins Phthalocyanines* 2000, 4, 564.
14. Bishop, S. M.; Khoo, B. J.; MacRobert, A. J.; Simpson, M. S. C.; Phllips, D.; Beeby, A. *J. Chromatogr.* 1993, 646, 345.
15. Rocha Gonsalves, A. M. A.; Johnson, R. A. W.; Pereira, M. M.; SantAna, A. M. P.; Serra, A. C.; Sobral, A. J. F. N. *Heterocycles* 1996, 43, 829. (b) Vinagradov, S. A.; Wilson, D. F. *J. Chem, Soc. Perkin* 2, 1995, 103. (c) Bishop, S. M.; Khoo, B. J.; MacRobert, A. J.; Simpson, M. S. C.; Phillips, D.; Beeby, A. *J. Chromatogr.* 1993, 646, 345.
16. Meier-Callahan, A. E.; Simkhovich, L; DiBilio, A. J.; Gray, H. B.; Goldberg, I; Gross, Z. *Inorg. Chem.* 2001, 40, 6788–6793. Mahammed, A.; Giladi, I.; Goldberg, I.; Gross, Z. *Chem. Eur. J.* 2001, 7, 4259. Meier-Callahan, A. E.; Gray, H. B.; Gross, Z. *Inorg. Chem.*, 2000, 39, 3605–3607. Simkhovich, L; Galili, N.; Saltsman, I.; Goldberg, I.; Gross, Z. *Inorg. Chem.* 2000, 39, 2704–5.
17. Sheldrick, G. M. SHELXS-86, *Acta Crystallogr.* 1990, A46, 467; Altomare, A.; Burla, M. C.; Camalli, M.; Cascarano, M.; Giacovazzo, C.; Guagliardi, A.; Polidori, G. SIR-92, *J. Appl. Crystallogr.* 1994, 27, 435.
18. Sheldrick, G. M. SHELXL-97. Program for the Refinement of Crystal Structures from Diffraction Data, University of Goettingen, Germany, 1997.

What is claimed is:
1. A corrole of formula I:

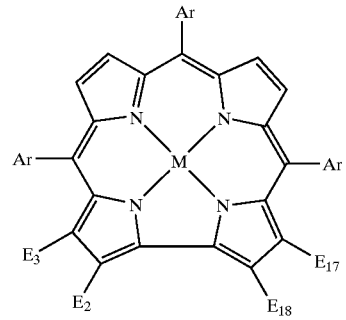

wherein:

Ar is aryl or heteroaryl;

M is absent or is a metal selected from the group consisting of Al, Ga, Co, Mn, Fe, Ru, Sn, Cr and Rh;

$E_2$, $E_3$ and $E_{17}$, the same or different, each is H, $SO_2Cl$, $SO_3H$, $SO_2NR_1R_2$, $CO_2H$, $CO_2R$, COCl, $CONR_1R_2$, CHO or $NO_2$, R is alkyl or aryl, and $R_1$ and $R_2$, the same or different, each is H, alkyl, aryl or together with the N atom to which they are attached form a saturated 5–6 membered ring optionally containing a further heteroatom selected from the group consisting of O, S and N; and $E_{18}$ is H or CHO; or $E_3$ and $E_{18}$ each is H and $E_2$ and $E_{17}$ each is $SO_2$, both $SO_2$ groups being linked by a bridge $R_3N(R_4)$-phenyl-$(R_4)NR_3$, wherein $R_3$ is H, alkyl, phenyl or aralkyl, and $R_4$ is alkylene; and provided that at least one of $E_2$, $E_3$, $E_{17}$ and $E_{18}$ is not H.

2. A corrole of claim 1, wherein Ar is selected from the group consisting of 2,6-dichlorophenyl, 2,6-difluorophenyl, pentafluorophenyl, 4-methoxy-2,3,5,6-tetrafluorophenyl, 4-(pyrid-2-yl)-2,3,5,6-tetrafluorophenyl, and 4-(N-methyl-pyrid-2-ylium)-2,3,5,6-tetrafluorophenyl.

3. A corrole of claim 1, wherein $E_3$ and $E_{18}$ each is H and $E_2$ and $E_{17}$ each is $SO_2Cl$, $SO_3H$ or $SO_2NR_1R_2$, or $E_2$ and $E_{18}$ each is H and $E_3$ and $E_{17}$ each is $SO_2Cl$, $SO_3H$ or $SO_2NR_1R_2$, wherein $R_1$ and $R_2$, the same or different, each is H, alkyl, aryl or together with the N atom to which they are attached form a saturated 5–6 membered ring optionally containing a further heteroatom selected from the group consisting of O, S and N.

4. A corrole of claim 3, selected from the group of compounds consisting of:

2,17-Bis(chlorosulfonyl)-5,10,15-tris(pentafluorophenyl) corrole;

3,17-Bis(chlorosulfonyl)-5,10,15-tris(pentafluorophenyl) corrole;

5,10,15-Tris(pentafluorophenyl)-2,17-bis(sulfonic acid)-corrole;

5,10,15-Tris(pentafluorophenyl)-3,17-bis(sulfonic acid)-corrole;

2,17-Bis(piperidinosulfonyl)-5,10,15-tris(pentafluorophenyl)corrole; and 3,17-Bis(piperidinosulfonyl)-5,10,15-tris(pentafluorophenyl)corrole.

5. A corrole of claim 1, wherein $E_3$ and $E_{18}$ each is H and $E_2$ and $E_{17}$ each is $SO_2$, both $SO_2$ groups being linked by a bridge $R_3N(R_4)$-phenyl-$(R_4)NR_3$, wherein $R_4$ is —$CH_2$— and $R_3$ is isopropyl or phenetyl.

6. A metallated corrole of claim 3, selected from the group of compounds consisting of:
- 2,17-Bis(piperidinosulfonyl)-5,10,15-tris (pentafluorophenyl)corrolato cobalt(III) (triphenylphosphine);
- 2,17-Bis(piperidinosulfonyl)-5,10,15-tris (pentafluorophenyl)corrolato rhodium(III) (triphenylphosphine);
- 3,17-bis(piperidinosulfonyl)-5,10,15-tris (pentafluorophenyl)corrolato cobalt(III) (triphenylphosphine);
- 5,10,15-Tris(pentafluorophenyl)-2,17-bis(sulfonic acid) corrolato gallium(III) (pyridine);
- 5,10,15-Tris(pentafluorophenyl)-2,17-bis(sulfonic acid)-corrolato manganese(III);
- 5,10,15-Tris(pentafluorophenyl)-2,17-bis(sulfonic acid)-corrolato cobalt (III) (triphenylphosphine);
- 5,10,15-Tris(pentafluorophenyl)-2,17-bis(sulfonic acid)-corrolato tin(IV) (chloro);
- 5,10,15-Tris(pentafluorophenyl)-2,17-bis(sulfonic acid)-corrolato chromium(III) (pyridine)$_2$; and
- 5,10,15-Tris(pentafluorophenyl)-2,17-bis(sulfonic acid)-corrolato iron(III).

7. A corrole of claim 1, wherein either $E_3$ is $NO_2$ and $E_2$, $E_{17}$ and $E_{18}$ each is H; or $E_3$ and $E_{17}$ each is $NO_2$ and $E_2$ and $E_{18}$ each is H; or $E_3$, $E_{17}$ and $E_{18}$ each is $NO_2$ and $E_2$ is H.

8. A corrole of claim 7, selected from the group of compounds consisting of:
- 3-Nitro-5,10,15-tris(pentafluorophenyl)corrolato gallium (III) pyridine)$_2$;
- 3,17-Dinitro-5,10,15-tris(pentafluorophenyl)corrolato gallium(III) pyridine)$_2$;
- 3,17,18-Trinitro-5,10,15-tris(pentafluorophenyl)corrolato gallium(III) (pyridine)$_2$; and
- 3-Nitro-5,10,15-tris(pentafluorophenyl)corrolato tin(IV) (chloride).

9. A corrole of claim 1, wherein either $E_{18}$ is CHO and $E_2$, $E_3$ and $E_{17}$ each is H; or $E_2$ and $E_{17}$ each is CHO and $E_3$ and $E_{18}$ each is H; or $E_2$, $E_3$ and $E_{17}$ each is CHO and $E_{18}$ is H.

10. A corrole of claim 9, selected from the group of compounds consisting of:
- 3-Formyl-5,10,15-tris(pentafluorophenyl)corrolato gallium(III) (pyridine);
- 2,17-Bis(formyl)-5,10,15-tris(pentafluorophenyl) corrolato gallium(III) (pyridine);
- 3-Formyl-5,10,15-tris(pentafluorophenyl)corrolato aluminum(III) (pyridine)$_2$;
- 2,17-Bis(formyl)-5,10,15-tris(pentafluorophenyl) corrolato aluminum(III) (pyridine)$_2$;
- 3-Formyl-5,10,15-tris(pentafluorophenyl)corrolato manganese (III) (pyridine);
- 2,17-Bis(formyl)-5,10,15-tris(pentafluorophenyl) corrolato manganese(III) (pyridine);
- 2,17-Bisformyl-5,10,15-tris(pentafluorophenyl)corrolato cobalt (III) (pyridine)$_2$; and
- 2,3,17-Trisformyl-5,10,15-tris(pentafluorophenyl) corrolato cobalt(III) (pyridine)$_2$.

11. A corrole of claim 1, wherein $E_3$ is COCl, COOH or COOR, wherein R is alkyl, and $E_2$, $E_{17}$, and $E_{18}$ each is H.

12. A corrole of claim 11, selected from the group of compounds consisting of:
- 3-chlorocarbonyl-5,10,15-tris(pentafluorophenyl) corrolato gallium(III) (pyridine);
- 5,10,15-Tris(pentafluorophenyl)corrolato gallium(III) (pyridine) 3-carboxylic acid; and
- 5,10,15-Tris(pentafluorophenyl)corrolato gallium(III) (pyridine) 3-carboxylic acid methyl ester.

13. A process for the preparation of a compound of claim 1 wherein $E_3$ and $E_{18}$ each is H arid $E_2$ and $E_{17}$ each is $SO_2Cl$, which comprises chlorosulfonation of 5,10,15-tris (pentafluorophenyl)corrole by reaction with chlorosulfonic acid, thus obtaining the 2,17-bis(chlorosulfonyl)-5,10,15-tris(pentafluorophenyl)corrole.

14. A process for the preparation of a compound of claim 1 wherein $E_3$ and $E_{18}$ each is H and $E_2$ and $E_{17}$ each is $SO_3H$ or $E_2$ and $E_{18}$ each is H and $E_3$ and $E_{17}$ each is $SO_3H$, which comprises either hydrolysis of 2,17-bis(chlorosulfonyl)-5, 10,15-tris(pentafluorophenyl)corrole thus obtaining the desired 5,10,15-tris(pentafluorophenyl)-2,17 bis(sulfonic acid)corrole, or direct sulfonation of 5,10,15-tris (pentafluorophenyl)corrole with $E_2SO_4$ thus obtaining the desired 5,10,15-tris(pentafluorophenyl)-2,17-bis(sulfonic acid)corrole and 5,10,15-tris(pentafluorophenyl)-3,17 bis (sulfonic acid)corrole.

15. A process for the preparation of a compound of claim 1, wherein $E_3$ and $E_{18}$ each is H and $E_2$ and $E_{17}$ each is $SO_2NR_1R_2$, or $E_2$ and $E_{18}$ each is H and $E_3$ and $E_{17}$ each is $SO_2NR_1R_2$, wherein $R_1$ and $R_2$, the same or different, each is H, alkyl, aryl or together with the N atom to which they are attached form a saturated 5–6 membered ring optionally containing a further heteroatom selected from the group consisting of O, S and N, which comprises amidation of 2,17-bis(chlorosulfonyl)-5,10,15-tris(pentafluorophenyl) corrole or of 3,17-bis (chlorosulfonyl)-5,10,15-tris (pentafluorophenyl)corrole with an amine $HNR_1R_2$, wherein $R_1$ and $R_2$, the same or different, each is H, alkyl, aryl or together with the N atom to which they are attached form a saturated 5–6 membered ring optionally containing a further heteroatom selected from the group consisting of O, S and N.

16. A process according to claim 15 wherein said amine $HNR_1R_2$ is piperidine, thus obtaining 2,17-bis (piperidinosulfonyl)-5,10,15-tris(pentafluorophenyl)corrole or 3,17-bis(piperidinosulfonyl)-5,10,15-tris (pentafluorophenyl)corrole.

17. A process for preparing a metal complex of a corrole of claim 3, which comprises reacting the unmetallated corrole of claim 3 with a metal acetate, wherein the metal is selected from the group consisting of Cr, Fe, Mn, Co, Ga and Sn.

18. A process according to claim 17, wherein the unmetallated corrole is 5,10,15-tris(pentafluorophenyl)-2,17-bis (sulfonic acid)corrole.

19. A process for selective nitration of 5,10,15-tris (pentafluorophenyl)corrole, which comprises reacting the gallium or tin complex of 5,10,15-tris(pentafluorophenyl) corrole in the presence of 0.7–2 equivalents of an oxidant, whereby in the presence of <0.7 equivalents of oxidant, the gallium complex of 3-nitro-5,10,15-tris(pentafluorophenyl) corrole is obtained, and in the presence of 2 equivalents of oxidant, the gallium complex of 3,17-dinitro-5,10,15-tris (pentafluorophenyl)corrole is obtained along with a small amount of 2,3,17-trinitro-5,10,15-tris(pentafluorophenyl) corrole.

20. A process according to claim 19 wherein the oxidant is tris(4-bromophenyl)aluminium hexachloroantimonate.

21. A process for selective formylation of the gallium, manganese, cobalt or aluminum complex of 5,10,15-tris (pentafluorophenyl)corrole, which comprises reacting 5,10, 15-tris(pentafluorophenyl)corrole in the presence of 1–10 equivalents of Vilsmeier reagent (POCl₃ and DMF) followed by hydrolysis, whereby in the presence of 1 equivalent of reagent, the gallium complex of 3-formyl-5,10,15-tris(pentafluorophenyl)corrole is obtained, and in the presence of excess reagent, the gallium complex of 2,3,17-triformyl-5,10,15-tris(pentafluorophenyl)corrole is obtained.

22. A pharmaceutical composition comprising a pharmaceutically acceptable carrier and a corrole of claim 1 selected from the group consisting of:

- 5,10,15-tris(pentafluorophenyl)corrole-2,17-bis(sulfonic acid);
- 5,10,15-tris(pentafluorophenyl)corrole-3,17-bis(sulfonic acid);
- 5,10,15-Tris(pentafluorophenyl)-2,17-bis(sulfonic acid) corrolato gallium(III) (pyridine);
- 5,10,15-Tris(pentafluorophenyl)-2,17-bis(sulfonic acid)-corrolato manganese(III);
- 5,10,15-Tris(pentafluorophenyl)-2,17-bis(sulfonic acid)-corrolato cobalt(III) (triphenylphosphine);
- 5,10,15-Tris(pentafluorophenyl)-2,17-bis(sulfonic acid)-corrolato chromium(III) (pyridine)₂;
- 5,10,15-Tris(pentafluorophenyl)-2,17-bis(sulfonic acid)-corrolato iron(III);
- 5,10,15-Tris(pentafluorophenyl)corrolato gallium(III) (pyridine) 3-carboxylic acid; and
- 5,10,15-Tris(pentafluorophenyl)corrolato gallium(III) (pyridine) 3-carboxylic acid methyl ester.

23. A pharmaceutical composition according to claim 22 for treatment of tumors in combination with light, wherein the corrole is selected from the group consisting of:

- 5,10,15-tris(pentafluorophenyl)corrole-2,17-bis(sulfonic acid);
- 5,10,15-tris(pentafluorophenyl)corrole-3,17-bis(sulfonic acid);
- 5,10,15-Tris(pentafluorophenyl)-2,17-bis(sulfonic acid) corrolato gallium(III) (pyridine);
- 5,10,15-Tris(pentafluorophenyl)-3,17-bis(sulfonic acid)-corrolato manganese(III);
- 5,10,15-Tris(pentafluorophenyl)-2,17-bis(sulfonic acid)-corrolato cobalt(III) (triphenylphosphine);
- 5,10,15-Tris(pentafluorophenyl)-2,17-bis(sulfonic acid)-corrolato chromium(III) (pyridine)₂;
- 5,10,15-Tris(pentafluorophenyl)-2,17-bis(sulfonic acid)-corrolato iron(III);
- 5,10,15-Tris(pentafluorophenyl)corrolato gallium(III) (pyridine) 3-carboxylic acid; and
- 5,10,15-Tris(pentafluorophenyl)corrolato gallium(III) (pyridine) 3-carboxylic acid methyl ester.

24. A pharmaceutical composition according to claim 22 for treatment of tumors in the absence of light, wherein the corrole is selected from the group consisting of:

- 5,10,15-Tris(pentafluorophenyl)-2,17-bis(sulfonic acid) corrolato gallium(III) (pyridine); and
- 5,10,15-Tris(pentafluorophenyl)-2,17-bis(sulfonic acid)-corrolato manganese(III).

25. A pharmaceutical composition according to claim 22 for tumor detection by fluorescence techniques, wherein the corrole is selected from the group consisting of:

- 5,10,15-tris(pentafluorophenyl)corrole-2,17-bis(sulfonic acid);
- 5,10,15-tris(pentafluorophenyl)corrole-3,17-bis(sulfonic acid);
- 5,10,15-Tris(pentafluorophenyl)-2,17-bis(sulfonic acid) corrolato gallium(III) (pyridine);
- 5,10,15-Tris(pentafluorophenyl)corrolato gallium(III) (pyridine) 3-carboxylic acid; and
- 5,10,15-Tris(pentafluorophenyl)corrolato gallium(III) (pyridine) 3-carboxylic acid methyl ester.

* * * * *